United States Patent
Sasaki

(10) Patent No.: US 11,053,553 B2
(45) Date of Patent: Jul. 6, 2021

(54) DETECTION OF CLDN18-ARHGAP6 FUSION GENE OR CLDN18-ARHGAP26 FUSION GENE IN PANCREATIC CANCER

(71) Applicants: Astellas Pharma Inc., Tokyo (JP); National Cancer Center, Tokyo (JP)

(72) Inventor: Hiroki Sasaki, Chuo-ku (JP)

(73) Assignees: Astellas Pharma Inc., Tokyo (JP); National Cancer Center, Tokyo (JP)

( * ) Notice: Subject to any disclaimer, the term of this patent is extended or adjusted under 35 U.S.C. 154(b) by 15 days.

(21) Appl. No.: 16/324,366

(22) PCT Filed: Aug. 9, 2017

(86) PCT No.: PCT/JP2017/028906
§ 371 (c)(1),
(2) Date: Feb. 8, 2019

(87) PCT Pub. No.: WO2018/030459
PCT Pub. Date: Feb. 15, 2018

(65) Prior Publication Data
US 2019/0218620 A1    Jul. 18, 2019

(30) Foreign Application Priority Data

Aug. 10, 2016 (JP) .................................. 2016-157167

(51) Int. Cl.
*C12Q 1/68* (2018.01)
*C07H 21/04* (2006.01)
*C12Q 1/6886* (2018.01)
*C12N 15/09* (2006.01)

(52) U.S. Cl.
CPC ........... *C12Q 1/6886* (2013.01); *C12N 15/09* (2013.01); *C12Q 1/68* (2013.01); *C12Q 2600/106* (2013.01)

(58) Field of Classification Search
None
See application file for complete search history.

(56) References Cited

FOREIGN PATENT DOCUMENTS

WO    WO 2004/074510 A1    9/2004
WO    WO 2015/142293 A1    9/2015

OTHER PUBLICATIONS

The Cancer Genome Atlas Research Network, Nature, Sep. 11, 2014, vol. 513, pp. 202-209. (Year: 2014).*
Karanjawala et al. Am. J. Surg. Pathol. 2008. vol. 32, No. 2, pp. 188-196 (Year: 2008).*
Ge et al. (Bioinformatics, vol. 27, No. 14, pp. 1922-1928, 2011) (Year: 2011).*
A. Karanjawala et al. (Am. J. Surg Pathol, vol. 32, No. 2, pp. 188-196, 2008) (Year: 2008).*
B. Yao et al. (Cell Reports, vol. 12, 272-285, Jul. 14, 2015) (Year: 2015).*
Supplementary European Search Report dated Feb. 13, 2020, in EP 17839527.3.
Sahin et al., "Claudin-18 Splice Variant 2 is a Pan-Cancer Target Suitable for Therapeutic Antibody Development," Clinical Cancer Research, Dec. 1, 2008, 14(23):7624-7634.
Ushiku et al., "RHOA mutation in diffuse-type gastric cancer: a comparative clinicopathology analysis of 87 cases," Gastric Cancer, 2016 (online Apr. 1, 2015), 19(2):403-411.
Wong et al., "Genomic landscape and genetic heterogeneity in gastric adenocarcinoma revealed by whole-genome sequencing," Nature Communications, Nov. 19, 2014, 5(5477), 12 pages.
Zhu et al., "Targeting CLDN18.2 by CD3 Bispecific and ADC Modalities for the Treatments of Gastric and Pancreatic Cancer," Scientific Reports, Jun. 10, 2019, 9(1), 11 pages.
International Search Report dated Oct. 24, 2017, in PCT/JP2017/028906.
The Cancer Genome Atlas Research Network, "Comprehensive molecular characterization of gastric adenocarcinoma," Nature, Sep. 11, 2014, 513:202-209.
Karanjawala et al., "New Markers of Pancreatic Cancer Identified Through Differential Gene Expression Analyses: Claudin 18 and Annexin A8," Am. J. Surg., Pathol., Feb. 2008, 32(2):188-196.
Yao et al., "Recurrent Fusion Genes in Gastric Cancer: CLDN18-ARHGAP26 Induces Loss of Epithelial Integrity," Cell Reports, Jul. 14, 2015, 12:272-285.

* cited by examiner

*Primary Examiner* — Jeanine A Goldberg
(74) *Attorney, Agent, or Firm* — Foley & Lardner LLP

(57) ABSTRACT

The purpose is to reveal a polynucleotide that is a novel causal gene of pancreatic cancer and thereby provide a method for detecting the polynucleotide or a polypeptide encoded thereby to select a subject positive for the polynucleotide or polypeptide and a method expected to be useful for to identify patients suitable for therapies and a primer set therefor and a kit for detection. In the method, a polynucleotide comprising a fusion point of a part of a CLDN18 gene and an ARHGAP6 gene or a polynucleotide comprising a fusion point of a part of a CLDN18 gene and an ARHGAP26 gene, or a fusion protein encoded thereby is detected. The primer set comprises a sense primer designed for a part encoding CLDN18 and an antisense primer designed for a part encoding ARHGAP6 or a part encoding ARHGAP26.

9 Claims, 4 Drawing Sheets
Specification includes a Sequence Listing.

Fig. 3

| Sample No. | Fusion gene | Sequence (5' → 3') | SEQ ID NO |
|---|---|---|---|
| No.164 | CLDN18-ARHGAP26 | CAAGAAGAATATACGATGGAGGTGGGGGGAAGAAGGAGAAAGAAAGAAAGAGAGACAGTAAAGGAAGTACTG | SEQ ID NO:17 |
| No.170 | CLDN18-ARHGAP6 | CAAGAAGAATATACGATGGATGGATCGGGCGATTCAGTGGAAAGGGATTTGCAGTGTGAGAAAGACATGTAC | SEQ ID NO:18 |
| No.192 | CLDN18-ARHGAP6 | CAAGAAGAATATACGATGGATGGATCGGGCGATTCAGTGGAAAGGGATTTGCAGTGTGAGAAAGACATGTAC | SEQ ID NO:18 |
| No.193 | CLDN18-ARHGAP6 | CAAGAAGAATATACGATGGATGGATCGGGCGATTCAGTGGAAAGGGATTTGCAGTGTGAGAAAGACATGTAC | SEQ ID NO:18 |
| No.197 | CLDN18-ARHGAP6 | CAAGAAGAATATACGATGGATGGATCGGGCGATTCAGTGGAAAGGGATTTGCAGTGTGAGAAAGACATGTAC | SEQ ID NO:18 |
| No.204 | CLDN18-ARHGAP6 | CAAGAAGAATATACGATGGATGGATCGGGCGATTCAGTGGAAAGGGATTTGCAGTGTGAGAAAGACATGTAC | SEQ ID NO:18 |
| No.205 | CLDN18-ARHGAP6 | CAAGAAGAATATACGATGGATGGATCGGGCGATTCAGTGGAAAGGGATTTGCAGTGTGAGAAAGACATGTAC | SEQ ID NO:20 |
| No.209 | CLDN18-ARHGAP6 | CAAGAAGAATATACGATGGATGGATCGGGCGATTCAGTGGAAAGGGATTTGCAGTGTGAGAAAGACATGTAC | SEQ ID NO:19 |
| No.210 | CLDN18-ARHGAP6 | CAAGAAGAATATACGATGGATGGATCGGGCGATTCAGTGGAAAGGGATTTGCAGTGTGAGAAAGACATGTAC | SEQ ID NO:21 |
| No.230 | CLDN18-ARHGAP6 | CAAGAAGAATATACGATGGATGGATCGGGCGATTCAGTGGAAAGGGATTTGCAGTGTGAGAAAGACATGTAC | SEQ ID NO:21 |

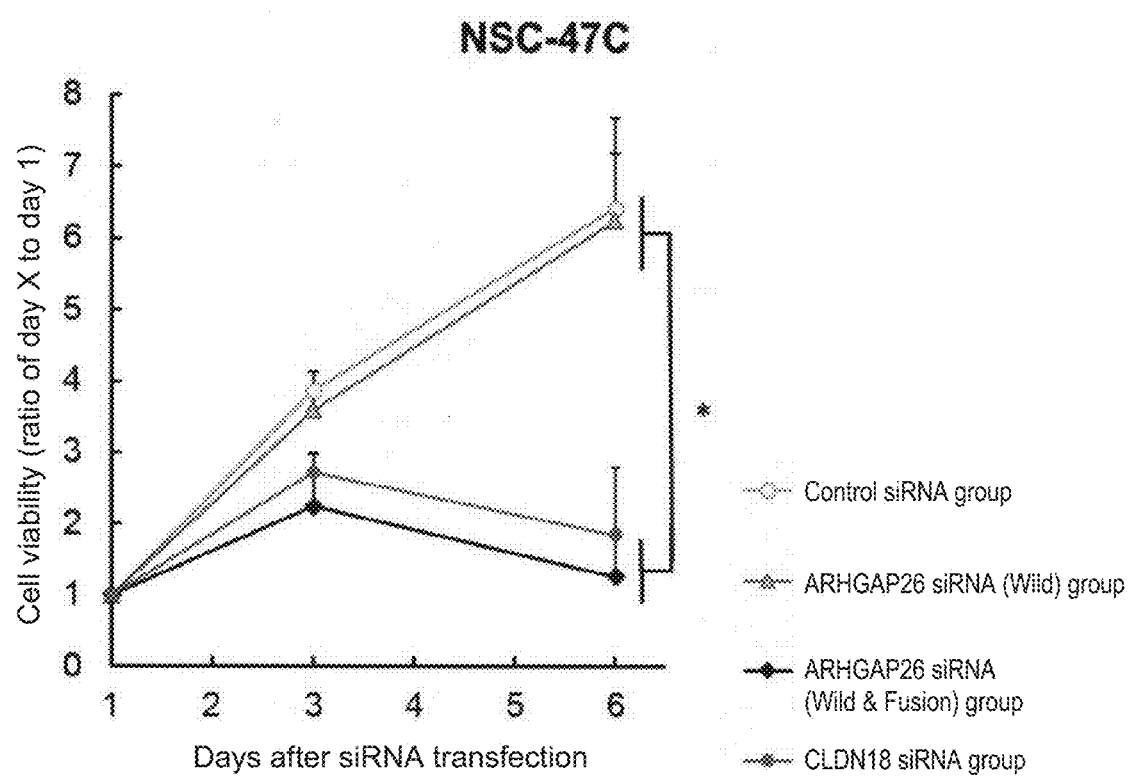

DETECTION OF CLDN18-ARHGAP6 FUSION GENE OR CLDN18-ARHGAP26 FUSION GENE IN PANCREATIC CANCER

CROSS-REFERENCE TO RELATED APPLICATIONS

This application is the U.S. National Stage of PCT/JP2017/028906, filed Aug. 9, 2017, which claims priority to JP 2016-157167 filed Aug. 10, 2016 and JP 2016-221434 filed Nov. 14, 2016.

The instant application contains a Sequence Listing which has been submitted in ASCII format via EFS-WEB and is hereby incorporated by reference in its entirety. Said ASCII copy, created on Feb. 7, 2019, is named sequence.txt and is 76 KB.

TECHNICAL FIELD

The present invention relates to the detection of CLDN18-ARHGAP6 fusion gene or CLDN18-ARHGAP26 fusion gene.

BACKGROUND ART

Claudin-18 (CLDN18) gene is located on the long arm of human chromosome 3 and a protein encoded by this gene is a four-transmembrane protein. As to its function, this protein has been expected to contribute to the cellular attachment by tight junction because it has been reported that claudin 1 (CLDN1) and claudin 2 (CLDN2), which belong to the same gene family, each forms complexes with occludin (OCLN), which is also a four-transmembrane protein, to constitute tight junction (J Cell Biol., 1998; 143 (2): 391-401) and that CLDN18 gene-knockout mice had aberrant structure of the tight junction between gastric epithelial cells, and also suffered from gastritis due to leak of gastric juice into the tissue (Gastroenterology, 2012; 142 (2): 292-304). With respect to cancer, it has been reported that the expression level of CLDN18.2, which is one of the splicing variants, was elevated in various cancers (Clin Cancer Res. 2008; 14 (23): 7624-7634), while it has also been reported that gastric cancer patients with high CLDN18 expression levels have better prognoses (Int J Surg. 2014; 12 (2): 156-162).

Rho GTPase activating protein 26 (ARHGAP26) gene, a GTPase activator, is located on the long arm of human chromosome 5 and a protein encoded by this gene is GTPase activating protein having a Rho-GAP domain at the middle. As to its function, it is known that the protein increases GTP hydrolase activity of the small GTPase protein family, in particular, ras homolog family member A (RhoA) and cell division cycle 42 (CDC42) (J Biol Chem., 2000; 275 (49): 38605-38610). With respect to cancer, ARHGAP26 has been found in gastric cancer (PTL 1) and, in particular, its fusion gene with CLDN18 gene has been found in 3% of gastric cancer (NPL 1) and, in particular, 15% of poorly differentiated gastric cancer patients (NPL 2), respectively in primary lesions. In addition, its fusion gene with mixed-lineage leukemia (MLL) gene has been found in leukemia patients (Proc Natl Acad Sci USA., 2000; 97 (16): 9168-9173, Genes Chromosomes Cancer, 2004; 41 (4): 400-404).

Rho GTPase activating protein 6 (ARHGAP6) gene, a GTPase activator, is located on the short arm of human X chromosome and encodes a GTPase activating protein having a Rho-GAP domain in the middle, like ARHGAP26 described above. As to its function, it is known that the protein also increases, like ARHGAP26, GTP hydrolase activity of the small GTPase protein family, in particular, RhoA (Hum Mol Genet., 2000; 9 (4): 477-488). With respect to cancer, its fusion gene with CLDN18 gene described above was found in primary lesions in patients suffered from poorly differentiated gastric cancer, although with a small percentage (NPL 2).

Currently, the fusion gene of CLDN18 and ARHGAP26 and the fusion gene of CLDN18 and ARHGAP6 have not been reported in any other cancer types except to gastric cancer. For example, the article published in Nature, 2016; 531: 47-52, reported results of mutation analysis in pancreatic cancer specimens, in which they reported that mutations in 32 genes were recurrently detected in pancreatic cancer specimens and pancreatic cancer cell lines (n=456). However, they also reported that any fusion genes were not detected recurrently, and if detected, in just one specimen ("No recurrent fusion events were detected"). Besides, they did not mention about the fusion gene of CLDN18 and ARHGAP26, or the fusion gene of CLDN18 and ARHGAP6.

CITATION LIST

Patent Literature

PTL 1: International Publication No. WO 2015/142293

Non Patent Literature

NPL 1: Cell Rep., 2015; 12 (2): 272-285
NPL 2: Nature, 2014; 513 (7517): 202-209

SUMMARY OF INVENTION

Technical Problem

The purpose of the present invention is to reveal a polynucleotide that is a novel causal gene for pancreatic cancer, and thereby to provide methods to select subject positive for the polynucleotide or the encoded polypeptide by detecting them, methods expected to be useful to identify patients suitable for therapies, primer sets, probes, probe sets, or kits for the detection therefor.

Solution to Problem

The present inventor found that a polynucleotide comprising a fusion point between a part of CLDN18 gene and a part of ARHGAP6 gene, or a polynucleotide comprising a fusion point between a part of CLDN18 gene and a part of ARHGAP26 gene, can be detected in pancreatic cancer patients (Example 1). Based on the finding, the present inventor constructed a step to detect a polynucleotide comprising a fusion point of the fusion gene, provided primer sets therefor, and enabled to provide a method expected to allow selection of pancreatic cancer patients positive for a fusion gene of CLDN18 gene and ARHGAP6 gene, or a fusion gene of CLDN18 gene and ARHGAP26 gene by detecting a polynucleotide comprising a fusion point of the aforementioned fusion gene.

Accordingly, the present invention relates to the following [1] to [25].

[1] A method for selecting a subject positive for a fusion gene of Claudin-18 (CLDN18) gene and Rho GTPase Activating Protein 6 (ARHGAP6) gene or a subject positive for a fusion gene of Claudin-18 (CLDN18) gene and Rho GTPase Activating Protein 26 (ARHGAP26) gene, comprising a step of detecting the presence of a polynucleotide comprising a fusion point of CLDN18 gene and ARHGAP6 gene or a polynucleotide comprising a fusion point of CLDN18 gene and ARHGAP26 gene in a sample from a subject suspected to have pancreatic cancer or a subject having pancreatic cancer.

[2] The method according to [1], wherein the polynucleotide is polynucleotide encoding a polypeptide of (1) or (2) as follows:

(1) a polypeptide comprising an amino acid sequence having 90% or more identity with an amino acid sequence set forth in SEQ ID NO: 2, 4, 6, or 8;

(2) a polypeptide having an amino acid sequence modified from an amino acid sequence set forth in SEQ ID NO: 2, 4, 6, or 8 by deletion, substitution, insertion, and/or addition of 1 to 10 amino acids.

[3] The method according to [2], wherein the polypeptide of (1) or (2) has tumor promoting ability.

[4] The method according to [2], wherein the polynucleotide is a polynucleotide encoding a polypeptide consisting of an amino acid sequence set forth in SEQ ID NO: 2, 4, 6, or 8.

[5] The method according to [1], wherein the polynucleotide is a polynucleotide of (3) or (4) as follows:

(3) a polynucleotide comprising a nucleotide sequence having 90% or more identity with a nucleotide sequence set forth in SEQ ID NO: 17 or 19;

(4) a polynucleotide comprising a nucleotide sequence modified from a nucleotide sequence set forth in SEQ ID NO: 17 or 19 by deletion, substitution, insertion, and/or addition of 1 to 10 nucleotides.

[6] The method according to [5], wherein the polynucleotide is a polynucleotide consisting of a nucleotide sequence set forth in SEQ ID NO: 17, 18, 19, 20, or 21.

[7] The method according to any of [1] to [6], further comprising a step of determining that the subject is a subject positive for a fusion gene of CLDN18 gene and ARHGAP6 gene or a subject positive for a fusion gene of CLDN18 gene and ARHGAP26 gene when the presence of the polynucleotide is detected, and determining that the subject is not a subject positive for the fusion gene when the presence of the polynucleotide is not detected.

[8] The method according to any of [1] to [7], comprising a step of amplifying a nucleic acid in a sample obtained from the subject and/or hybridizing a probe with a nucleic acid in a sample obtained from the subject for detecting the presence of the polynucleotide.

[9] The method according to [8], comprising a step of amplifying a nucleic acid in a sample obtained from the subject using a primer set as follows:

a primer set for detecting the fusion gene of the CLDN18 gene and the ARHGAP6 gene or the fusion gene of the CLDN18 gene and the ARHGAP26 gene, comprising a sense primer designed for a part encoding CLDN18 and an antisense primer designed for a part encoding ARHGAP6 or a part encoding ARHGAP26, wherein the antisense primer consists of an oligonucleotide that hybridizes with the polynucleotide under stringent conditions and the sense primer consists of an oligonucleotide that hybridizes with a complementary strand to the polynucleotide under stringent conditions.

[10] The method according to [9], wherein the sense primer consists of an oligonucleotide that hybridizes with a complementary strand to the polynucleotide consisting of nucleotides at positions 1 to 750 in SEQ ID NO: 1 under stringent conditions, and the antisense primer consists of an oligonucleotide that hybridizes with the polynucleotide consisting of nucleotides at positions 751 to 3087 in SEQ ID NO: 1 under stringent conditions;

the sense primer consists of an oligonucleotide that hybridizes with a complementary strand to the polynucleotide consisting of nucleotides at positions 1 to 750 in SEQ ID NO: 3 under stringent conditions, and the antisense primer consists of an oligonucleotide that hybridizes with the polynucleotide consisting of nucleotides at positions 751 to 2460 in SEQ ID NO: 3 under stringent conditions;

the sense primer consists of an oligonucleotide that hybridizes with a complementary strand to the polynucleotide consisting of nucleotides at positions 1 to 750 in SEQ ID NO: 5 under stringent conditions, and the antisense primer consists of an oligonucleotide that hybridizes with the polynucleotide consisting of nucleotides at positions 751 to 2088 in SEQ ID NO: 5 under stringent conditions; or the sense primer consists of an oligonucleotide that hybridizes with a complementary strand to the polynucleotide consisting of nucleotides at positions 1 to 750 in SEQ ID NO: 7 under stringent conditions, and the antisense primer consists of an oligonucleotide that hybridizes with the polynucleotide consisting of nucleotides at positions 751 to 1923 in SEQ ID NO: 7 under stringent conditions.

[11] The method according to [9] or [10], wherein the sense primer consists of an oligonucleotide of at least any 16 consecutive bases between nucleotides at positions 1 to 750 in SEQ ID NO: 1, and the antisense primer consists of an oligonucleotide complementary to an oligonucleotide of at least any 16 consecutive bases between nucleotides at positions 751 to 3087 in SEQ ID NO: 1;

the sense primer consists of an oligonucleotide of at least any 16 consecutive bases between nucleotides at positions 1 to 750 in SEQ ID NO: 3, and the antisense primer consists of an oligonucleotide complementary to an oligonucleotide of at least any 16 consecutive bases between nucleotides at positions 751 to 2460 in SEQ ID NO: 3;

the sense primer consists of an oligonucleotide of at least any 16 consecutive bases between nucleotides at positions 1 to 750 in SEQ ID NO: 5, and the antisense primer consists of an oligonucleotide complementary to an oligonucleotide of at least any 16 consecutive bases between nucleotides at positions 751 to 2088 in SEQ ID NO: 5; or the sense primer consists of an oligonucleotide of at least any 16 consecutive bases between nucleotides at positions 1 to 750 in SEQ ID NO: 7, and the antisense primer consists of an oligonucleotide complementary to an oligonucleotide of at least any 16 consecutive bases between nucleotides at positions 751 to 1923 in SEQ ID NO: 7.

[12] The method according to any of [9] to [11], further comprising a step of determining whether an amplified nucleic acid fragment with an intended size is obtained.

[13] The method according to [12], further comprising a step of determining that the subject is a subject positive for a fusion gene of CLDN18 gene and ARHGAP6 gene or a subject positive for a fusion gene of CLDN18 gene and ARHGAP26 gene when the amplified nucleic acid fragment with the intended size is obtained, and determining that the subject is not a subject positive for the fusion gene when the fragment is not obtained.

[14] The method according to any of [9] to [11], further comprising a step of determining the nucleotide sequence of the amplified nucleic acid fragment.

[15] The method according to [14], further comprising a step of determining the subject is a subject positive for a fusion gene of CLDN18 gene and ARHGAP6 gene or a subject positive for a fusion gene of CLDN18 gene and ARHGAP26 gene when the amplified nucleic acid fragment comprises the nucleotide sequence of a part encoding CLDN18 and the nucleotide sequence of a part encoding ARHGAP6 or the nucleotide sequence of a part encoding ARHGAP26 in the same fragment, and determining that the subject is not a subject positive for the fusion gene when the nucleotide sequences are not comprised in the same fragment.

[16] The method according to [8], comprising a step of hybridizing a probe comprising an oligonucleotide that hybridizes with the polynucleotide under stringent conditions with a nucleic acid in a sample obtained from the subject.

[17] The method according to [16], comprising a step of performing in situ hybridization using a sample obtained from the subject, a probe designed for a part encoding CLDN18 in the polynucleotide, and a probe designed for a part encoding ARHGAP6 or a part encoding ARHGAP26 in the polynucleotide.

[18] The method according to [17], involving use of a plurality of probes designed for a part encoding CLDN18 and a plurality of probes designed for a part encoding ARHGAP6 or a part encoding ARHGAP26.

[19] The method according to [17] or [18], involving use of a plurality of flanking probe pairs comprising an oligonucleotide complementary to an oligonucleotide of at least any 16 consecutive bases of nucleotides at positions 1 to 750 in SEQ ID NO: 1, and a plurality of flanking probe pairs comprising an oligonucleotide complementary to an oligonucleotide of at least any 16 consecutive bases of nucleotides at positions 751 to 3087 in SEQ ID NO: 1;

use of a plurality of flanking probe pairs comprising an oligonucleotide complementary to an oligonucleotide of at least any 16 consecutive bases of nucleotides at positions 1 to 750 in SEQ ID NO: 3, and a plurality of flanking probe pairs comprising an oligonucleotide complementary to an oligonucleotide of at least any 16 consecutive bases of nucleotides at positions 751 to 2460 in SEQ ID NO: 3;

use of a plurality of flanking probe pairs comprising an oligonucleotide complementary to an oligonucleotide of at least any 16 consecutive bases of nucleotides at positions 1 to 750 in SEQ ID NO: 5, and a plurality of flanking probe pairs comprising an oligonucleotide complementary to an oligonucleotide of at least any 16 consecutive bases of nucleotides at positions 751 to 2088 in SEQ ID NO: 5; or use of a plurality of flanking probe pairs comprising an oligonucleotide complementary to an oligonucleotide of at least any 16 consecutive bases of nucleotides at positions 1 to 750 in SEQ ID NO: 7, and a plurality of flanking probe pairs comprising an oligonucleotide complementary to an oligonucleotide of at least any 16 consecutive bases of nucleotides at positions 751 to 1923 in SEQ ID NO: 7, in the step of hybridizing a probe with a nucleic acid in the sample obtained from the subject.

[20] The method according to any of [17] to [19], further comprising a step of amplifying a signal of the hybridization.

[21] The method according to any of [17] to [20], further comprising a step of detecting an overlap of a signal from a probe designed for a part encoding CLDN18 and a signal from a probe designed for a part encoding ARHGAP6 or a part encoding ARHGAP26.

[22] The method according to [21], further comprising a step of determining that the subject is a subject positive for a fusion gene of CLDN18 gene and ARHGAP6 gene or a subject positive for a fusion gene of CLDN18 gene and ARHGAP26 gene when the presence of the two signals at the same location is detected, and determining that the subject is not a subject positive for the fusion gene when the presence of the two signals at the same location is not detected.

[23] The method according to any of [1] to [22], comprising a step of obtaining a sample from the subject.

[24] The method according to any of [1] to [23], wherein the sample is body fluid or body cavity lavage fluid.

[25] The method according to any of [1] to [24], wherein the sample is ascites or peritoneal cavity lavage fluid.

Moreover, the present invention relates to the following [26] to [31].

[26] A method for identifying a subject suspected to have pancreatic cancer or a subject having pancreatic cancer that is an indication for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene, comprising a step according to any of [1] to [22].

[27] The method according to [26], comprising a step of obtaining a sample from the subject.

[28] The method according to [26] or [27], further comprising a step of determining that the subject is suitable for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene when a polynucleotide comprising the fusion point of the CLDN18 gene and the ARHGAP6 gene or a polynucleotide comprising the fusion point of the CLDN18 gene and the ARHGAP26 gene is detected in a sample obtained from the subject, and determining that the subject is not suitable for the therapy when the polypeptide is not detected.

[29] The method according to [26] or [27], further comprising the step according to [12] and a step of determining that the subject is suitable for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene when an amplified nucleic acid fragment with the intended size is obtained, and determining that the subject is not suitable for the therapy when the amplified nucleic acid fragment is not obtained.

[30] The method according to [26] or [27], further comprising the step according to [14] and a step of determining that the subject is suitable for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene when the amplified nucleic acid fragment comprises the nucleotide sequence of a part encoding CLDN18 and the nucleotide sequence of a part encoding ARHGAP6 or the nucleotide sequence of a part encoding ARHGAP26 in the same fragment, and determining that the subject is not suitable for the therapy when the amplified nucleic acid fragment does not comprise the nucleotide sequences.

[31] The method according to [26] or [27], further comprising the step according to [21] and a step of determining that the subject is suitable for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene when the presence of the two signals at the same location is detected, and determining that the subject is not suitable for the therapy when the presence of the two signals at the same location is not detected.

Moreover, the present invention relates to the following [32] to [34].

[32] A primer set for detecting the fusion gene of the CLDN18 gene and the ARHGAP6 gene or the fusion gene of the CLDN18 gene and the ARHGAP26 gene in a sample from a subject suspected to have pancreatic cancer or a subject having pancreatic cancer, comprising a sense primer designed for a part encoding CLDN18 and an antisense primer designed for a part encoding ARHGAP6 or a part encoding ARHGAP26, wherein the antisense primer consists of an oligonucleotide that hybridizes with the polynucleotide according to any of [1] to [6] under stringent conditions and the sense primer consists of an oligonucleotide that hybridizes with a complementary strand to the polynucleotide under stringent conditions.

[33] The primer set according to [32], wherein
the sense primer consists of an oligonucleotide that hybridizes with a complementary strand to the polynucleotide consisting of nucleotides at positions 1 to 750 in SEQ ID NO: 1 under stringent conditions, and the antisense primer consists of an oligonucleotide that hybridizes with the polynucleotide consisting of nucleotides at positions 751 to 3087 in SEQ ID NO: 1 under stringent conditions;
the sense primer consists of an oligonucleotide that hybridizes with a complementary strand to the polynucleotide consisting of nucleotides at positions 1 to 750 in SEQ ID NO: 3 under stringent conditions, and the antisense primer consists of an oligonucleotide that hybridizes with the polynucleotide consisting of nucleotides at positions 751 to 2460 in SEQ ID NO: 3 under stringent conditions;
the sense primer consists of an oligonucleotide that hybridizes with a complementary strand to the polynucleotide consisting of nucleotides at positions 1 to 750 in SEQ ID NO: 5 under stringent conditions, and the antisense primer consists of an oligonucleotide that hybridizes with the polynucleotide consisting of nucleotides at positions 751 to 2088 in SEQ ID NO: 5 under stringent conditions; or
the sense primer consists of an oligonucleotide that hybridizes with a complementary strand to the polynucleotide consisting of nucleotides at positions 1 to 750 in SEQ ID NO: 7 under stringent conditions, and the antisense primer consists of an oligonucleotide that hybridizes with the polynucleotide consisting of nucleotides at positions 751 to 1923 in SEQ ID NO: 7 under stringent conditions.

[34] The primer set according to [32] or [33], wherein
the sense primer consists of an oligonucleotide of at least any 16 consecutive bases between nucleotides at positions 1 to 750 in SEQ ID NO: 1, and the antisense primer consists of an oligonucleotide complementary to an oligonucleotide of at least any 16 consecutive bases between nucleotides at positions 751 to 3087 in SEQ ID NO: 1;
the sense primer consists of an oligonucleotide of at least any 16 consecutive bases between nucleotides at positions 1 to 750 in SEQ ID NO: 3 and the antisense primer consists of an oligonucleotide complementary to an oligonucleotide of at least any 16 consecutive bases between nucleotides at positions 751 to 2460 in SEQ ID NO: 3;
the sense primer consists of an oligonucleotide of at least any 16 consecutive bases between nucleotides at positions 1 to 750 in SEQ ID NO: 5, and the antisense primer consists of an oligonucleotide complementary to an oligonucleotide of at least any 16 consecutive bases between nucleotides at positions 751 to 2088 in SEQ ID NO: 5; or
the sense primer consists of an oligonucleotide of at least any 16 consecutive bases between nucleotides at positions 1 to 750 in SEQ ID NO: 7, and the antisense primer consists of an oligonucleotide complementary to an oligonucleotide of at least any 16 consecutive bases between nucleotides at positions 751 to 1923 in SEQ ID NO: 7.

Moreover, the present invention relates to the following [35] to [38].

[35] A probe for detecting a fusion gene of CLDN18 gene and ARHGAP6 gene or a fusion gene of CLDN18 gene and ARHGAP26 gene in a sample from a subject suspected to have pancreatic cancer or a subject having pancreatic cancer, comprising an oligonucleotide that hybridizes with the polynucleotide according to any of [1] to [6] under stringent conditions.

[36] A probe set comprising a plurality of probes according to [35], comprising a probe designed for a part encoding CLDN18 and a probe designed for a part encoding ARHGAP6 or a part encoding ARHGAP26 in the polynucleotide according to any of [1] to [6].

[37] The probe set according to [36], comprising a plurality of probes designed for a part encoding CLDN18 and a plurality of probes designed for a part encoding ARHGAP6 or a part encoding ARHGAP26.

[38] A probe set of [36] or [37], comprising
a plurality of flanking probe pairs comprising an oligonucleotide complementary to an oligonucleotide of at least any 16 consecutive bases of nucleotides at positions 1 to 750 in SEQ ID NO: 1, and a plurality of flanking probe pairs comprising an oligonucleotide complementary to an oligonucleotide of at least any 16 consecutive bases of nucleotides at positions 751 to 3087 in SEQ ID NO: 1
a plurality of flanking probe pairs comprising an oligonucleotide complementary to an oligonucleotide of at least any 16 consecutive bases of nucleotides at positions 1 to 750 in SEQ ID NO: 3, and a plurality of flanking probe pairs comprising an oligonucleotide complementary to an oligonucleotide of at least any 16 consecutive bases of nucleotides at positions 751 to 2460 in SEQ ID NO: 3;
a plurality of flanking probe pairs comprising an oligonucleotide complementary to an oligonucleotide of at least any 16 consecutive bases of nucleotides at positions 1 to 750 in SEQ ID NO: 5, and a plurality of flanking probe pairs comprising an oligonucleotide complementary to an oligonucleotide of at least any 16 consecutive bases of nucleotides at positions 751 to 2088 in SEQ ID NO: 5; or
a plurality of flanking probe pairs comprising an oligonucleotide complementary to an oligonucleotide of at least any 16 consecutive bases of nucleotides at positions 1 to 750 in SEQ ID NO: 7, and a plurality of flanking probe pairs comprising an oligonucleotide complementary to an oligonucleotide of at least any 16 consecutive bases of nucleotides at positions 751 to 1923 in SEQ ID NO: 7.

Moreover, the present invention relates to following [39] to [41].

[39] A kit for detecting a fusion gene of CLDN18 gene and ARHGAP6 gene or a fusion gene of CLDN18 gene and ARHGAP26 gene in a sample from a subject suspected to have pancreatic cancer or a subject having pancreatic cancer, comprising the primer set according to any of [32] to [34],

[40] A kit for detecting a fusion gene of CLDN18 gene and ARHGAP6 gene or a fusion gene of CLDN18 gene and ARHGAP26 gene in a sample obtained from a subject suspected to have pancreatic cancer or a subject having pancreatic cancer, comprising a probe or the probe set according to any of [35] to [38],

[41] A kit for detection according to [40], further comprising a reagent for amplifying a signal of the hybridization.

Moreover, the present invention relates to the following [42] to [47].

[42] A method for selecting a subject positive for fusion protein of CLDN18 and ARHGAP6 or a subject positive for a fusion protein of CLDN18 and ARHGAP26, comprising a step of detecting the presence of a polypeptide of the following (1) or (2) in a sample obtained from a subject suspected to have pancreatic cancer or a subject having pancreatic cancer:
(1) a polypeptide comprising an amino acid sequence having 90% or more identity with an amino acid sequence set forth in SEQ ID NO: 2, 4, 6, or 8;
(2) a polypeptide having an amino acid sequence modified from an amino acid sequence set forth in SEQ ID NO: 2, 4, 6, or 8 by deletion, substitution, insertion, and/or addition of 1 to 10 amino acids.

[43] The method according to [42], wherein the polypeptide has tumor promoting ability.

[44] The method according to [42], wherein the polypeptide is a polypeptide consisting of an amino acid sequence set forth in SEQ ID NO: 2, 4, 6, or 8.

[45] The method according to any of [42] to [44], wherein the step of detecting the presence of the polypeptide comprises a step of bringing an antibody (primary antibody) that recognizes a part derived from the CLDN18 gene in the polypeptide and an antibody (primary antibody) that recognizes a part derived from the ARHGAP6 gene or a part derived from the ARHGAP26 gene in the polypeptide in contact with the sample obtained from the subject.

[46] The method according to [45], further comprising the steps of i) to v) as follows:
i) a step of adding oligonucleotide-conjugated secondary antibodies that respectively bind to the primary antibodies;
ii) a step of adding a ligation solution containing 2 oligonucleotides partially complementary to the oligonucleotides conjugated to the secondary antibodies and a ligase capable of ligating the 2 oligonucleotides when they come in the vicinity to form a ring structure and making ligation to cause a ligation reaction; iii) a step of extending a nucleic acid along the formed ring structure; iv) a step of hybridizing a labelled oligonucleotide probe capable of hybridizing the extended nucleic acid; and v) a step of detecting the label signal.

[47] The method according to any of [42] to [46], comprising a step of obtaining a sample from the subject.

Moreover, the present invention relates to the following [48] to [50].

[48] A method for identifying a subject suspected to have pancreatic cancer or a subject having pancreatic cancer that is an indication for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene, comprising a step according to any of [42] to [46].

[49] The method according to [48], comprising a step of obtaining a sample from the subject.

[50] The method according to [48] or [49], further comprising a step of determining that the subject is suitable for a therapy with an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene when the polypeptide according to any of [42] to [44] is detected in a sample obtained from the subject, and determining that the subject is not suitable for the therapy when the polypeptide is not detected.

Moreover, the present invention relates to the following [51] to [52].

[51] A kit for detecting a fusion protein of CLDN18 and ARHGAP6 or a fusion protein of CLDN18 and ARHGAP26 in a sample obtained from a subject suspected to have pancreatic cancer or a subject having pancreatic cancer, comprising an antibody (primary antibody) that recognizes a part derived from the CLDN18 gene in the polypeptide according to any of [42] to [44] and an antibody (primary antibody) that recognizes a part derived from the ARHGAP6 gene or a part derived from the ARHGAP26 gene in the polypeptide.

[52] A kit for detection according to [51], comprising oligonucleotide-conjugated secondary antibodies that respectively bind to the primary antibodies, 2 oligonucleotides partially complementary to the oligonucleotides conjugated to the secondary antibodies, a ligase capable of ligating the 2 oligonucleotides when they are in the vicinity to form a ring structure, a polymerase capable of extending a nucleic acid along the ring structure, and a labelled oligonucleotide probe.

Moreover, the present invention relates to the following [53].

[53] A polypeptide according to the following (1) or (2) or a polynucleotide encoding the polypeptide:
(1) a polypeptide comprising an amino acid sequence having 90% or more identity with an amino acid sequence set forth in SEQ ID NO: 2, 4, 6, or 8;
(2) a polypeptide having an amino acid sequence modified from an amino acid sequence set forth in SEQ ID NO: 2, 4, 6, or 8 by deletion, substitution, insertion, and/or addition of 1 to 10 amino acids.

Moreover, the present invention relates to the following [54].

[54] A polypeptide according to any of the following (1) to (3) or a polynucleotide encoding the polypeptide:
(1) a polypeptide comprising an amino acid sequence having 90% or more identity with the amino acid sequence set forth in SEQ ID NO: 2, 4, 6, or 8 and having tumor promoting ability;
(2) a polypeptide comprising the amino acid sequence set forth in SEQ ID NO: 2, 4, 6, or 8 and having tumor promoting ability or a polypeptide having an amino acids sequence modified from the amino acid sequence set forth in SEQ ID NO: 2, 4, 6, or 8 by deletion, substitution, insertion, and/or addition of 1 to 10 amino acids and having tumor promoting ability;
(3) a polypeptide consisting of the amino acid sequence set forth in SEQ ID NO: 2, 4, 6, or 8.

Advantageous Effects of Invention

The method according to the present invention is expected to be useful to detect pancreatic cancer positive for a fusion gene of CLDN18 gene and ARHGAP6 gene or a fusion gene of CLDN18 gene and ARHGAP26 gene (hereinafter, also referred to as "CLDN18-ARHGAP6 fusion gene", "CLDN18-ARHGAP26 fusion gene", "CLDN18-ARHGAP6/26 fusion gene", or "fusion gene of the present invention"), or to identify subjects for therapies with agents that blocks signals induced by a fusion gene indicated in the present invention. The primer sets, probes, probe sets, and kits for detection of the present invention can be used in the method according to the present invention.

BRIEF DESCRIPTION OF DRAWINGS

FIG. 3 shows the result of nucleotide sequencing of the regions containing the fusion point of CLDN18-ARHGAP6/26 fusion gene product amplified by PCR. The underlined region indicates a sequence corresponding to ARHGAP6 or ARHGAP26.

FIG. 6 shows the result of cell viability assay confirming that the viability of a gastric cancer cell line NSC-47C were attenuated significantly by treating the gastric cancer cell line with an siRNA targeting CLDN18-ARHGAP26 fusion gene.

DESCRIPTION OF EMBODIMENTS

Method According to the Present Invention

Figure 1:
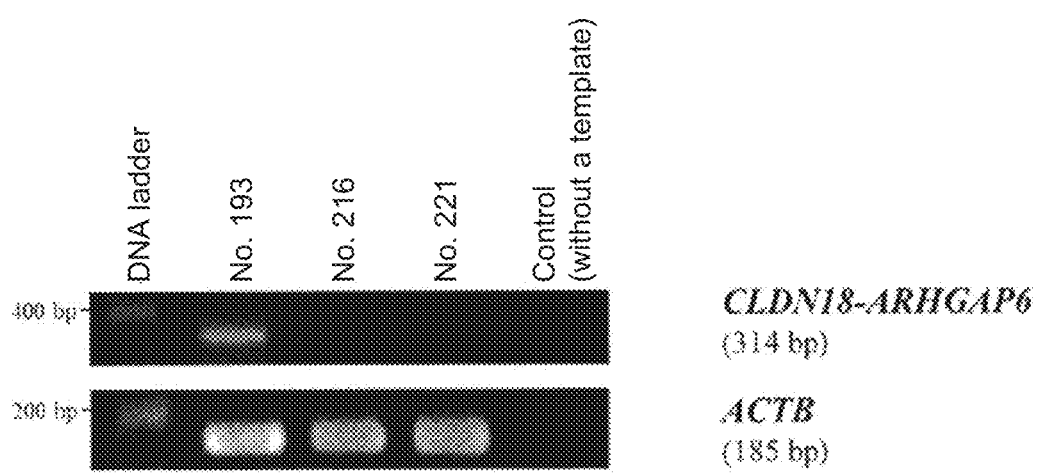
FIG. 1 shows the result of electrophoresis of PCR products which were amplified the region containing a fusion point of CLDN18-ARHGAP6 fusion gene by PCR from cDNA, as a template, prepared from total RNA purified from ascites of pancreatic cancer patients.

The method according to the present invention includes 1. a method for selecting a subject positive for a fusion gene, and 2. a method for selecting a subject positive for a fusion protein encoded by a fusion gene (collectively hereinafter also referred to as the "selection method according to the present invention"). Furthermore, the method according to the present invention includes 3. a method for identifying a subject for which a therapy with an ARHGAP6 inhibitor or an ARHGAP26 inhibitor and/or an agent that blocks an abnormal signal induced by a fusion gene of CLDN18 gene and ARHGAP6 gene or a fusion gene of the CLDN18 gene and ARHGAP26 gene is suitable (hereinafter also referred to as the "identification method according to the present invention"). The method according to the present invention includes a step of detecting the presence of a particular polynucleotide or polypeptide in a sample obtained from a subject.

In the method according to the present invention, a sample obtained from a subject may be a collected material from a subject (a sample separated from a living body), such as any collected cell, tissue, body fluid, and body cavity lavage fluid. It is preferable to use ascites which is body fluid, and peritoneal lavage fluid which is body cavity lavage fluid. It is particularly preferable to use ascites. As the body cavity lavage fluid, it may be used lavage fluid which is obtained by introducing lavage fluid (e.g. saline) into a subject's body cavity (peritoneal or the like) during laparotomy or by catheterization, performing a lavage of the body cavity, and then collecting the lavage fluid. It is known that such lavage fluid is provided for cytology. From the sample obtained from a subject, genomic DNA may be extracted to be used. Alternatively, a transcription product thereof (a resulting product of the transcription or translation of the genomic DNA; e.g., RNA or protein) or cDNA prepared from the RNA may be used. In particular, it is preferable to prepare and use RNA or cDNA. The sample may be used after subjecting a sample collected from a subject into a pretreatment such as dilution or concentration, a precipitation treatment by centrifugation, or an addition of a blood coagulation inhibitor such as heparin, as necessary. Alternatively, the sample may be used as it is without such a pretreatment. Further, the sample may be used as a stabilized specimen wherein a sample is formalin-fixed and embedded in paraffin (Formalin-Fixed Paraffin-Embedded sample; FFPE specimen). It may be used as a thinly sliced FFPE section of the FFPE specimen. With the FFPE section, it is possible to directly detect a polynucleotide or polypeptide present therein. In one embodiment, the method according to the present invention includes a step of obtaining a sample from a subject.

In the method according to the present invention, a "fusion gene of CLDN18 gene and ARHGAP6 gene" or a "fusion gene of CLDN18 gene and ARHGAP26 gene" refers to a fusion gene containing a part of a CLDN18 gene and a part of an ARHGAP6 gene, or a fusion gene containing a part of CLDN18 gene and a part of ARHGAP26 gene. Representative examples of the fusion gene of the CLDN18 gene and the ARHGAP6 gene include a polynucleotide consisting of a nucleotide sequence set forth in SEQ ID NO: 1 or a polynucleotide consisting of a nucleotide sequence set forth in SEQ ID NO: 3. Representative examples of the fusion gene of the CLDN18 gene and the ARHGAP26 gene include a polynucleotide consisting of a nucleotide sequence set forth in SEQ ID NO: 5 or a polynucleotide consisting of a nucleotide sequence set forth in SEQ ID NO: 7.

The polynucleotide consisting of the nucleotide sequence set forth in SEQ ID NO: 1 is a polynucleotide having a nucleotide sequence of nucleotides at positions 54 (corresponding to 5' end of the coding sequence (hereinafter referred to as CDS)) to 803 in CLDN18 gene (NCBI accession number: NM_001002026.2) and nucleotides at positions 1462 to 3798 in ARHGAP6 gene (NCBI accession number: NM_013427.2). The polynucleotide consisting of the nucleotide sequence set forth in SEQ ID NO: 3 is a polynucleotide having a nucleotide sequence of nucleotides at positions 54 (corresponding to 5' end of CDS) to 803 in CLDN18 gene (NCBI accession number: NM_001002026.2) and nucleotides at positions 1462 to 3171 in ARHGAP6 gene (NCBI accession number: NM_006125.2).

The polynucleotide consisting of the nucleotide sequence set forth in SEQ ID NO: 5 is a polynucleotide having a nucleotide sequence of nucleotides at positions 54 (corresponding to 5' end of CDS) to 803 in CLDN18 gene (NCBI accession number: NM_001002026.2) and nucleotides at positions 1143 to 2480 in ARHGAP26 gene (NCBI accession number: NM_015071.4)

The polynucleotide consisting of the nucleotide sequence set forth in SEQ ID NO: 7 is a polynucleotide having a nucleotide sequence of nucleotides at positions 54 (corresponding to 5' end of CDS) to 803 in CLDN18 gene (NCBI accession number: NM_001002026.2) and nucleotides at positions 1143 to 2315 in ARHGAP26 gene (NCBI accession number: NM_001135608.1).

In the nucleotide sequence set forth in SEQ ID NO: 1, a sequence of nucleotides at positions 1 to 750 is derived from the CLDN18 gene, and a sequence of nucleotides at positions 751 to 3087 is derived from the ARHGAP6 gene and, in the nucleotide sequence set forth in SEQ ID NO: 3, a sequence of nucleotides at positions 1 to 750 is derived from the CLDN18 gene, and a sequence of nucleotides at positions 751 to 2460 is derived from the ARHGAP6 gene. Meanwhile, in the nucleotide sequence set forth in SEQ ID NO: 5, a sequence of nucleotides at positions 1 to 750 is derived from the CLDN18 gene, and a sequence of nucleotides at positions 751 to 2088 is derived from the ARHGAP26 gene, and in the nucleotide sequence set forth in SEQ ID NO: 7, a sequence of nucleotides at positions 1 to 750 is derived from the CLDN18 gene, and a sequence of nucleotides at positions 751 to 1923 is derived from the ARHGAP26 gene.

The polynucleotide consisting of a nucleotide sequence set forth in SEQ ID NO: 1, 3, 5 or 7 is also referred to as a "fusion polynucleotide". The amino acid sequence encoded by nucleotides at positions 1 to 3087 in SEQ ID NO: 1 (including a stop codon) is set forth in SEQ ID NO: 2, and the amino acid sequence encoded by nucleotides at positions 1 to 2460 in SEQ ID NO: 3 (including a stop codon) is set forth in SEQ ID NO: 4. The amino acid sequence encoded by nucleotides at positions 1 to 2088 in SEQ ID NO: 5 (including a stop codon) is set forth in SEQ ID NO: 6, and the amino acid sequence encoded by nucleotides at positions 1 to 1923 in SEQ ID NO: 7 (including the stop codon) is set forth in SEQ ID NO: 8.

1. Method for Selecting a Subject Positive for a Fusion Gene

In the "step of detecting the presence of a polynucleotide" in the method for selecting a subject positive for a fusion gene according to the present invention (herein referred to as the "step of detecting the presence of a polynucleotide" according to the present invention), the polynucleotide to be used as the detection target (herein referred to as the "detection target polynucleotide") may be a polynucleotide containing a fusion point of CLDN18 gene and ARHGAP6 gene or a polynucleotide containing a fusion point of CLDN18 gene and ARHGAP26 gene. The "fusion point" in the detection target polynucleotide means a point in which a part derived from CLDN18 gene and a part derived from ARHGAP6 gene in the detection target polynucleotide are fused or in which a part derived from CLDN18 gene and a part derived from ARHGAP26 gene in the detection target polynucleotide are fused.

In one embodiment, the detection target polynucleotide may be a polynucleotide encoding a polypeptide of (1) or (2) as follows:
(1) a polypeptide comprising an amino acid sequence having 90% or more identity with an amino acid sequence set forth in SEQ ID NO: 2, 4, 6, or 8;
(2) a polypeptide having an amino acid sequence modified from an amino acid sequence set forth in SEQ ID NO: 2, 4, 6, or 8 by deletion, substitution, insertion, and/or addition of 1 to 10 amino acids.

The polypeptide may further have tumor promoting ability.

In the polypeptide, the "identity with an amino acid sequence set forth in SEQ ID NO: 2, 4, 6, or 8" is preferably 95% or more, more preferably 98% or more.

It should be noted that the "identity" used herein with reference to an amino acid sequence means a value Identity obtained by using parameters described below in a NEEDLE program (J Mol Biol. 1970; 48(3):443-453). The parameters are as follows:
Gap penalty=10
Extend penalty=0.5
Matrix=BLOSUM62

In the polypeptide, the amino acid sequence is modified from an amino acid sequence set forth in SEQ ID NO: 2, 4, 6, or 8 by deletion, substitution, insertion, and/or addition of 1 to several amino acids, preferably 1 to 10 amino acids, more preferably 1 to 7 amino acids, further preferably 1 to 5 amino acids.

Examples of the method for confirming that a polypeptide "has a tumor promoting ability" include a method having introducing an siRNA targeting a polynucleotide encoding the polypeptide into a cell capable of expressing the polypeptide, and then confirming that the viability of the cell decreases, as is exemplified by the method described in Reference Example 2.

In one embodiment, the detection target polynucleotide is a polynucleotide encoding a polypeptide of (1) or (2) as follows:
(1) a polypeptide having an amino acid sequence modified from an amino acid sequence set forth in SEQ ID NO: 2, 4, 6, or 8 by deletion, substitution, insertion, and/or addition of 1 to 10 amino acids and having tumor promoting ability;
(2) a polypeptide having an amino acid sequence set forth in SEQ ID NO: 2, 4, 6, or 8 and having tumor promoting ability.

In one embodiment, the detection target polynucleotide is a polynucleotide encoding a polypeptide consisting of an amino acid sequence set forth in SEQ ID NO: 2, 4, 6, or 8.

Examples of the polynucleotide encoding a "polypeptide consisting of an amino acid sequence set forth in SEQ ID NO: 2" include a "polynucleotide consisting of a nucleotide sequence set forth in SEQ ID NO: 1". Examples of the polynucleotide encoding a "polypeptide consisting of an amino acid sequence set forth in SEQ ID NO: 4" include a "polynucleotide consisting of a nucleotide sequence set forth in SEQ ID NO: 3". Examples of the polynucleotide encoding a "polypeptide consisting of an amino acid sequence set forth in SEQ ID NO: 6" include a "polynucleotide consisting of a nucleotide sequence set forth in SEQ ID NO: 5". Examples of the polynucleotide encoding a "polypeptide consisting of an amino acid sequence set forth in SEQ ID NO: 8" include a "polynucleotide consisting of a nucleotide sequence set forth in SEQ ID NO: 7". In one embodiment, the detection target polynucleotide is a polynucleotide consisting of a nucleotide sequence set forth in SEQ ID NO: 1, 3, 5 or 7.

Of the nucleotide sequence set forth in SEQ ID NO: 5 or 7, a sequence of nucleotides at positions 711 to 790 (a sequence having each 40 nucleotides of before and after the fusion point, a total of 80 nucleotides) is set forth in SEQ ID NO: 17. Of the nucleotide sequence set forth in SEQ ID NO: 1 or 3, a sequence of nucleotides at positions 711 to 790 (a sequence having each 40 nucleotides of before and after the fusion point, a total of 80 nucleotides) is set forth in SEQ ID NO: 19. The sequence modified from a sequence set forth in SEQ ID NO: 19 by single nucleotide substitution is a sequence set forth in SEQ ID NO: 18, 20, or 21.

In one embodiment, the detection target polynucleotide may be a polynucleotide of (3) or (4) as follows:
(3) a polynucleotide comprising a nucleotide sequence having 90% or more identity with a nucleotide sequence set forth in SEQ ID NO: 17 or 19;

(4) a polynucleotide comprising a nucleotide sequence modified from a nucleotide sequence set forth in SEQ ID NO: 17 or 19 by deletion, substitution, insertion, and/or addition of 1 to 10 nucleotides.

In the polynucleotide, the "identity with a nucleotide sequence set forth in SEQ ID NO: 17 or 19" is preferably 95% or more, and more preferably 98% or more.

It should be noted that the "identity" used herein with reference to a nucleotide sequence means a value Identity obtained by using parameters described below in a NEEDLE program (J Mol Biol. 1970; 48(3):443-453).

Gap penalty=10
Extend penalty=0.5
Matrix=DNA full

In the polynucleotide, the nucleotide sequence is modified from a nucleotide sequence set forth in SEQ ID NO: 17 or 19 by deletion, substitution, insertion, and/or addition of 1 to several nucleotides, preferably 1 to 10 nucleotides, more preferably 1 to 7 nucleotides, further preferably 1 to 5 nucleotides, still preferably 1 to 3 nucleotides, still more preferably 1 or 2 nucleotides. Examples of the sequence modified from a nucleotide sequence set forth in SEQ ID NO: 19 by single nucleotide substitution include a sequence set forth in SEQ ID NO: 18, 20, or 21.

In one embodiment, the detection target polynucleotide is a polynucleotide consisting of a nucleotide sequence set forth in SEQ ID NO: 17, 18, 19, 20, or 21.

The method for selecting a subject positive for a fusion gene according to the present invention may include either identifying a subject positive for a fusion gene of CLDN18 gene and ARHGAP6 gene or a fusion gene of CLDN18 gene and ARHGAP26 gene or identifying a subject negative for a fusion gene of a CLDN18 gene and ARHGAP6 gene or a fusion gene of CLDN18 gene and ARHGAP26 gene, or both.

In one embodiment, the method for selecting a subject positive for a fusion gene according to the present invention may further include a step of determining that the subject is a subject positive for a fusion gene of CLDN18 gene and ARHGAP6 gene or a subject positive for a fusion gene of CLDN18 gene and ARHGAP26 gene when the presence of the detection target polynucleotide is detected and determining that the subject is not a subject positive for the fusion gene when the presence of the detection target polynucleotide is not detected.

The method for selecting a subject positive for a fusion gene according to the present invention may include a step of amplifying a nucleic acid in a sample obtained from the subject (additional step A) and/or hybridizing a probe with a nucleic acid in a sample obtained from the subject (additional step B), for detecting the presence of detection target the polynucleotide.

The nucleic acid used may be a genomic DNA, RNA, or cDNA prepared from RNA. The methods for extraction of genomic DNA, extraction of RNA, and preparation of cDNA from RNA are known in the art, and they can be conveniently performed using a commercially available DNA extraction kit, RNA extraction kit, or cDNA synthesis kit.

The step of amplifying a nucleic acid in a sample obtained from the subject can be performed using a known nucleic acid amplification method. Examples of such a nucleic acid amplification method include PCR (Polymerase chain reaction, for example, real-time quantitative PCR), LCR (Ligase chain reaction), SDA (Strand displacement amplification), NASBA (Nucleic acid sequence-based amplification), ICAN (Isothermal and chimeric primer-initiated amplification of nucleic acids), LAMP (Loop-mediated isothermal amplification), and TMA (Transcription-mediated amplification). Preferred examples thereof include PCR.

Specifically, a nucleic acid in a sample obtained from a subject (for example, genomic DNA, RNA, or cDNA prepared from RNA) is subjected to a nucleic acid amplification reaction using a primer set designed to be capable of specifically amplifying the detection target polynucleotide, to be amplified. The primer set used is not particularly limited as long as it is capable of specifically amplifying the detection target polynucleotide. For example, such a primer set can be easily designed by those skilled in the art based on a nucleotide sequence of the detection target polynucleotide using a primer design software (for example, Primer Express®; Thermo Fisher Scientific K.K.) or the like. More specifically, the primer set contains a sense primer (5'-primer) designed for a part encoding CLDN18 in the detection target polynucleotide (e.g., any part within CLDN18 gene region of the fusion polynucleotide (particularly cDNA)) and an antisense primer (3'-primer) designed for a part encoding ARHGAP6 or a part encoding ARHGAP26 in the detection target polynucleotide (e.g., any part within ARHGAP6 or ARHGAP26 gene region of the fusion polynucleotide (particularly, cDNA)), wherein the antisense primer consists of an oligonucleotide that hybridizes with the detection target polynucleotide under stringent conditions (preferably, highly stringent conditions) and the sense primer consists of an oligonucleotide that hybridizes with a complementary strand to the detection target polynucleotide under stringent conditions (preferably, highly stringent conditions). Alternatively, one of the sense primer or antisense primer may be designed so as to correspond to a region containing a fusion point in the detection target polynucleotide.

The "stringent condition" used herein refers to a condition for hybridization of "5×SSPE, 5×Denhardt's solution, 0.5% SDS, 50% formamide, 200 µg/mL salmon sperm DNA, overnight at 42° C.", and a condition for washing of "0.5× SSC, 0.1% SDS, 42° C.". The "highly stringent condition" refers to a condition for hybridization of "5×SSPE, 5×Denhardt's solution, 0.5% SDS, 50% formamide, 200 µg/mL salmon sperm DNA, overnight at 42° C.", and a condition for washing of "0.2×SSC, 0.1% SDS, 65° C.".

As used herein, the "region containing a fusion point" in a detection target polynucleotide refers to, for example, a region containing nucleotides of nucleotides at positions 750 and 751 when the detection target polynucleotide is a polynucleotide consisting of a nucleotide sequence set forth in SEQ ID NO: 1, 3, 5 or 7, respectively. For example, the "region containing a fusion point" in the detection target polynucleotide refers to a region containing nucleotides of nucleotides at positions 40 and 41 when the detection target polynucleotide is a polynucleotide consisting of the nucleotide sequence set forth in SEQ ID NO: 17, 18, 19, 20 or 21, respectively.

In one embodiment, as a primer set, it is possible to use a primer set according to the present invention described below.

In a preferred embodiment, the method for selecting a subject positive for a fusion gene according to the present invention may further include, in addition to a step of amplifying a nucleic acid in a sample obtained from the subject, a step of determining whether an amplified nucleic acid fragment with an intended size is obtained (additional step C). The step of determining whether an amplified nucleic acid fragment with an intended size is obtained may be performed, for example, using electrophoresis. In the electrophoresis, for example, a nucleic acid fragment may be analyzed by agarose gel electrophoresis and stained by ethidium bromide or the like to confirm whether an amplified nucleic acid fragment with an intended size is obtained.

Further, by performing PCR amplification monitoring during the gene amplification process (real-time quantitative PCR) (Genome Res. 1996; 6(10):986-994), it is possible to make a more quantitative analysis for the amplified nucleic acid fragment. In the PCR amplification monitoring, for example, ABI PRISM® 7900 (Thermo Fisher Scientific K.K.) may be used.

When the amplified nucleic acid fragment with an intended size is obtained, it is considered that the detection target polynucleotide is present in a sample obtained from a subject. In one embodiment, the method for selecting a subject positive for a fusion gene according to the present invention may further include a step of determining that the subject is a subject positive for a fusion gene of CLDN18 gene and ARHGAP6 gene or a subject positive for a fusion gene of CLDN18 gene and ARHGAP26 gene when the amplified nucleic acid fragment with the intended size is obtained and determining that the subject is not a subject positive for the fusion gene when the fragment with the intended size is not obtained.

In another preferred embodiment, the method for selecting a subject positive for a fusion gene according to the present invention may further include, in addition to a step of amplifying a nucleic acid in a sample obtained from the subject, a step of determining the nucleotide sequence of the amplified nucleic acid fragment (additional step D). The step of determining the nucleotide sequence of the amplified nucleic acid fragment may be performed, for example, using a method known in the art such as a Sanger sequencing method (for example, ABI PRISM® 3100 (Thermo Fisher Scientific K.K.) may be used), and next-generation sequencing methods including a sequence by synthesis method (Nat Biotechnol. 2008; 26 (10): 1135-1145) (for example, HiSeq2500 (Illumina, Inc.) may be used).

The step of determining a nucleotide sequence of a nucleic acid fragment include not only a step of determining a sequence of the full length of the nucleic acid fragment, but also a step of determining a partial sequence containing both ends or a partial sequence containing a fusion point of the nucleic acid fragment.

When the sequenced nucleic acid fragment contains a nucleotide sequence of a part encoding CLDN18 and a nucleotide sequence of a part encoding ARHGAP6 or a nucleotide sequence of a part encoding ARHGAP26 in a detection target polynucleotide in the same fragment, it is considered that the detection target polynucleotide is present in the sample obtained from a subject. In one embodiment, the method for selecting a subject positive for a fusion gene according to the present invention may further include a step of determining the subject is a subject positive for a fusion gene of CLDN18 gene and ARHGAP6 gene or a subject positive for a fusion gene of CLDN18 gene and ARHGAP26 gene when the amplified nucleic acid fragment comprises the nucleotide sequence of a part encoding CLDN18 and the nucleotide sequence of a part encoding ARHGAP6 or the nucleotide sequence of a part encoding ARHGAP26 in the detection target polynucleotide in the same fragment and determining that the subject is not a subject positive for the fusion gene when the nucleotide sequences are not comprised in the same fragment.

The step of hybridizing a probe with a nucleic acid in a sample obtained from the subject may be performed using a known hybridization method using a probe comprising an oligonucleotide that hybridizes with the detection target polynucleotide under stringent conditions (preferably, highly stringent conditions). Examples of such a method include northern hybridization, a dot blot method, a DNA microarray method, an RNA protection method, and in situ hybridization. Preferred methods thereof include in situ hybridization. Detection using in situ hybridization techniques may be performed, for example, by a known method such as a fluorescence in situ hybridization (FISH) method, a chromogenic in situ hybridization (CISH) method, or a silver in situ hybridization (SISH) method. The chain length of a probe used in the hybridization may be appropriately selected by those skilled in the art depending on a hybridization method to be used, but the probe preferably has a chain length of at least 16 bases. In one embodiment, as a probe, it is possible to use a probe according to the invention described below.

In one embodiment, the step of hybridizing a probe with a nucleic acid in a sample obtained from the subject can be performed in accordance with a known RNA in situ hybridization (RNA ISH) method (J Mol Diagn. 2012; 14(1):22-29). More specifically, in situ hybridization is performed using a sample obtained from a subject (for example, ascites, peritoneal cavity lavage fluid, or the like), a probe designed for a part encoding CLDN18 in the detection target polynucleotide (e.g., any part within CLDN18 gene region of the fusion polynucleotide), and a probe designed for a part encoding ARHGAP6 or a part encoding ARHGAP26 in the detection target polynucleotide (e.g., any point within ARHGAP6 or ARHGAP26 gene region of the fusion polynucleotide). Each of the probe contains an oligonucleotide that hybridizes with the detection target polynucleotide under stringent conditions (preferably, highly stringent conditions).

In one embodiment, in situ hybridization is performed using a plurality of detection probes designed for a part encoding CLDN18 and a plurality of detection probes designed for a part encoding ARHGAP6 or a part encoding ARHGAP26.

In one embodiment, in situ hybridization is performed using a probe according to the present invention described below.

In a further embodiment, a probe pair used in situ hybridization may include a flanking probe pair comprising an oligonucleotide complementary to an oligonucleotide of at least any 16 consecutive bases in a 5'-untranslated region of CLDN18 gene (a region consisting of nucleotides at positions 1 to 53 in NCBI accession number: NM_001002026.2) and/or a flanking probe pair comprising an oligonucleotide complementary to an oligonucleotide of at least any 16 consecutive bases in a 3'-untranslated region of ARHGAP6 gene (a region consisting of nucleotides at positions 3799 to 5118 in NCBI accession number: NM_013427.2 or nucleotides at positions 3172 to 3632 in NCBI accession number: NM_006125.2) or in a 3'-untranslated region of ARHGAP26 gene (a region consisting of nucleotides at positions 2481 to 9041 in NCBI accession number: NM_015071.4 or nucleotides at positions 2316 to 8876 in NCBI accession number: NM_001135608.1).

As used herein, a "flanking probe pair" is composed of two probes hybridizing with the detection target polynucleotide side by side. Each of the probes contains an oligonucleotide complementary to the detection target polynucleotide, and the length of the oligonucleotide is typically at least 16 bases, preferably at least 18 bases. In one embodiment, the length of the oligonucleotide is 16 to 30 bases, preferably 18 to 25 bases.

In a preferred embodiment, the method for selecting a subject positive for a fusion gene according to the present invention may include, in addition to a step of performing in situ hybridization using a sample obtained from the subject, a step of amplifying a signal of the hybridization (additional step E). The step of amplifying a signal of the hybridization may be performed, for example, by hybridizing a reagent for amplifying the signal of the hybridization with a probe hybridized with a nucleic acid in a sample.

Examples of the reagent for amplifying the signal of the hybridization used during in situ hybridization include Pre-Amplifier Mix QT, Amplifier Mix QT, Label Probe Mix, and Label Probe Diluent QF, which are available from Affymetrix.

In a more preferred embodiment, the method for selecting a subject positive for a fusion gene according to the present invention further include a step of detecting an overlap of a signal from a probe designed for a part encoding CLDN18 and a signal from a probe designed for a part encoding ARHGAP6 or a part encoding ARHGAP26 (additional step F). By using different fluorescent or chromogenic reagents for detecting each of a probe designed for a part encoding CLDN18 and a probe designed for a part encoding ARHGAP6 or a part encoding ARHGAP26, it is possible to observe whether the signals from the two different probes are present at the same location (within the same molecule). When the presence of the two signals at the same location (within the same molecule) is detected, it is considered that the detection target polynucleotide is present in a sample obtained from the subject. In one embodiment, the method for selecting a subject positive for a fusion gene according to the present invention may further include a step of determining that the subject is a subject positive for a fusion gene of CLDN18 gene and ARHGAP6 gene or a subject positive for a fusion gene of CLDN18 gene and ARHGAP26 gene when the presence of the two signals at the same location (within the same molecule) is detected and determining that the subject is not a subject positive for the fusion gene when the presence of the two signals at the same location is not detected.

Each probe is not particularly limited. For example, the probe may be produced by a chemical synthesis method.

2. Method for Selecting Subject Positive for Fusion Protein Encoded by Fusion Gene The method for selecting a subject positive for a fusion protein according to the present invention is a method for detecting a subject positive for a "fusion protein of CLDN18 and ARHGAP6 or fusion protein of CLDN18 and ARHGAP26" (herein, referred to as the "fusion protein of the present invention"). The fusion protein is a fusion protein encoded by a fusion gene of CLDN18 gene and ARHGAP6 gene or a fusion protein encoded by a fusion gene of CLDN18 gene and ARHGAP26 gene.

Examples of the polypeptide to be detected in the "step of detecting the presence of a polypeptide" in the method for selecting a subject positive for a fusion protein according to the present invention (herein, referred to as the "step of detecting the presence of a polypeptide") (herein, referred to as the "polypeptide to be detected") include polypeptides encoded by polynucleotides to be detected.

The method for selecting a subject positive for a fusion protein according to the present invention may comprises either of identifying a subject positive for a fusion protein of CLDN18 and ARHGAP6 or a subject positive for a fusion protein of CLDN18 and ARHGAP26 and identifying a subject negative for a fusion protein of CLDN18 and ARHGAP6 or a subject negative for a fusion protein of CLDN18 and ARHGAP26.

The method for selecting a subject positive for a fusion protein according to the present invention may further comprises a step of determining that a subject is a subject positive for a fusion protein of CLDN18 and ARHGAP6 or a subject positive for a fusion protein of CLDN18 and ARHGAP26 when a polypeptide to be detected is detected and determining that a subject is not a subject positive for the fusion protein when the polypeptide is not detected.

For example, the step of detecting the presence of a polypeptide can be conducted by an immunological assay or an enzymatic activity assay or a combined method thereof for detection by preparing a lysate derived from a sample (for example, cancer tissue, cancer cells or body fluid such as ascites obtained from the subject) obtained from the subject and combining the polypeptide to be detected contained in the lysate with antibodies to the proteins composing the fusion protein or mass spectrometry. Moreover, this step may be conducted by a method for detection by an immunohistological staining technique by the combination of the polypeptide to be detected contained in a sample (for example, an FFPE section or a precipitate) obtained from the subject pretreated (for example, the removal of paraffin or centrifugation) as appropriate with antibodies to the proteins composing the fusion protein. Alternatively, this step may be conducted by a method modified from one of the methods of detection described above by replacing the antibodies to the proteins composing the fusion protein with an antibody that recognizes the fusion point in the fusion protein. Examples of such methods include methods such as enzyme immunoassay, double antibody sandwich ELISA (enzyme-linked immunosorbent assay), fluorescent immunoassay, radioimmunoassay, Western blotting, immunohistological staining, and a combined detection method of immunoprecipitation and mass spectrometry using a monoclonal antibody or a polyclonal antibody specific for a polypeptide to be detected.

As used herein, the "fusion point" of the fusion protein means a point in which a part derived from CLDN18 gene and a part derived from ARHGAP6 gene or a part derived from ARHGAP26 gene in the polypeptide to be detected are fused.

The detection using an immunohistological staining technique can be conducted, for example, by the proximity ligation assay (Nat Methods. 2006, 3 (12): 995-1000). More specifically, the presence of the polypeptide to be detected can be detected by detecting that the two antibodies recognize an identical molecule by the aforementioned techniques using an antibody that recognizes a part derived from CLDN18 gene in the polypeptide to be detected and an antibody that recognizes a part derived from ARHGAP6 gene or a part derived from ARHGAP26 gene in the polypeptide to be detected. More specifically, the detection can be conducted by i) a step of bringing an antibody (primary antibody) that recognizes a part derived from the CLDN18 gene in the polypeptide to be detected and an antibody (primary antibody) that recognizes a part derived from the ARHGAP6 gene or a part derived from the ARHGAP26 gene in the polypeptide to be detected in contact with the sample obtained from the subject; ii) a step of adding oligonucleotide-conjugated secondary antibodies that respectively bind to the primary antibodies; iii) a step of adding a ligation solution containing 2 oligonucleotides partially complementary to the oligonucleotides conjugated to the secondary antibodies and a ligase capable of ligating the 2 oligonucleotides when they come in the vicinity to form a ring structure to make ligation to cause a ligation reaction; iv) a step of extending a nucleic acid along the formed ring structure; v) a step of hybridizing a labelled oligonucleotide probe capable of hybridizing the extended nucleic acid; and vi) a step of detecting the label signal. Such detection can be conducted using a PLA probe and a reagent contained in Duolink® II reagent kit or Duolink® II Brightfield reagent kit (Olink Bioscience).

3. Method for Identification According to the Present Invention

Moreover, the "step of detecting the presence of a polynucleotide" according to the present invention and the "step of detecting the presence of a polypeptide" according to the present invention can be used in a method for identifying a subject (a patient with pancreatic cancer) for which a therapy is suitable for therapies by an ARHGAP6 inhibitor or an ARHGAP26 inhibitor and/or an agent that blocks an abnormal signal induced by the fusion gene of the CLDN18 gene and the ARHGAP6 gene or the fusion gene of the CLDN18 gene and the ARHGAP26 gene. Examples of the inhibitor of ARHGAP6 or ARHGAP26 include a function inhibitor or an expression inhibitor. Inhibiting a function refers to inhibiting a function of ARHGAP6 or ARHGAP26 as a protein. Inhibiting expression refers to inhibiting transcription and/or translation into a protein of a nucleic acid encoding the fusion gene according to the present invention or promoting the degradation of the protein. Examples of the abnormal signal induced by the fusion gene of the CLDN18 gene and the ARHGAP6 gene or the fusion gene of the CLDN18 gene and the ARHGAP26 gene include signals promoted or suppressed under the expression of these fusion genes in comparison with those under no expression of these fusion genes, for example, a signal that promotes the cell proliferation or a signal that suppresses programmed cell death. Examples of the agent that blocks an abnormal signal induced by the fusion gene of the CLDN18 gene and the ARHGAP6 gene or the fusion gene of the CLDN18 gene and the ARHGAP26 gene include an agent that downregulates a signal that promotes the cell proliferation or an agent that removes a signal that suppresses programmed cell death.

The method for identification according to the present invention may further comprise one or more steps (for example, one or more of the additional steps A to F) listed for the method for selection according to the present invention in addition to the step of detection. Furthermore, a primer set, a probe, a probe set, and a kit for detection used in the method for selecting according to the present invention may be used. Furthermore, the method for identification according to the present invention may comprise a step of determining, when a polynucleotide to be detected or a polypeptide to be detected is detected in a sample obtained from a subject, when the amplified nucleic acid fragment is obtained with an intended size, when the amplified nucleic acid fragment comprises the nucleotide sequence of a part encoding CLDN18 and the nucleotide sequence of a part encoding ARHGAP6 or the nucleotide sequence of a part encoding ARHGAP26 in the same fragment, or when two signals, a signal from a probe designed for a part encoding CLDN18 and a signal from a probe designed for a part encoding ARHGAP6 or a part encoding ARHGAP26, are detected in the same place (the same molecule), that the subject is suitable for a therapy with an ARHGAP6 inhibitor or an ARHGAP26 inhibitor; and/or an inhibitor of a fusion gene of CLDN18 gene and ARHGAP6 gene or a fusion gene of the CLDN18 gene and the ARHGAP26 gene, or an agent that blocks an abnormal signal induced by said fusion genes and determining that the subject is not suitable for the therapy when none of the above descriptions is true.

<Primer Set, Probe, Probe Set, and Kit for Detection According to the Present Invention>

The present invention comprises a primer set, a probe, a probe set, and a kit for detection used in the method according to the present invention.

The primer set according to the present invention comprises a sense primer designed for a part encoding CLDN18 and an antisense primer designed for a part encoding ARHGAP6 or a part encoding ARHGAP26, the antisense primer consists of an oligonucleotide that hybridizes with a polynucleotide to be detected under stringent conditions (preferably under highly stringent conditions), and the sense primer consists of an oligonucleotides that hybridizes with the complementary strand to the polynucleotide to be detected under stringent conditions (preferably under highly stringent conditions).

In the primer set according to the present invention, one of the sense primer or the antisense primer may be designed so that it corresponds to a region containing a fusion point in the polynucleotide to be detected.

Specific aspects of the primer set according to the present invention include the following primer sets:

a primer set of a sense primer consisting of an oligonucleotide that hybridizes with a complementary strand to the polynucleotide consisting of nucleotides at positions 1 to 750 in SEQ ID NO: 1 under stringent conditions and an antisense primer consisting of an oligonucleotide that hybridizes with the polynucleotide consisting of nucleotides at positions 751 to 3087 in SEQ ID NO: 1 under stringent conditions;

a primer set of a sense primer consisting of an oligonucleotide that hybridizes with a complementary strand to the polynucleotide consisting of nucleotides at positions 1 to 750 in SEQ ID NO: 3 under stringent conditions and an antisense primer consisting of an oligonucleotide that hybridizes with the polynucleotide consisting of nucleotides at positions 751 to 2460 in SEQ ID NO: 3 under stringent conditions;

a primer set of a sense primer consisting of an oligonucleotide that hybridizes with a complementary strand to the polynucleotide consisting of nucleotides at positions 1 to 750 in SEQ ID NO: 5 under stringent conditions and an antisense primer consisting of an oligonucleotide that hybridizes with the polynucleotide consisting of nucleotides at positions 751 to 2088 in SEQ ID NO: 5 under stringent conditions; or a primer set of a sense primer consisting of an oligonucleotide that hybridizes with a complementary strand to the polynucleotide consisting of nucleotides at positions 1 to 750 in SEQ ID NO: 7 under stringent conditions and an antisense primer consisting of an oligonucleotide that hybridizes with the polynucleotide consisting of nucleotides at positions 751 to 1923 in SEQ ID NO: 7 under stringent conditions.

More specific aspects of the primer set according to the present invention include the following primer sets:

a primer set of a sense primer consisting of at least any 16 consecutive bases between nucleotides at positions 1 to 750 in SEQ ID NO: 1 and an antisense primer consisting of an oligonucleotide complementary to an oligonucleotide of at least any 16 consecutive bases between nucleotides at positions 751 to 3087 in SEQ ID NO: 1;

a primer set of a sense primer consisting of at least any 16 consecutive bases between nucleotides at positions 1 to 750 in SEQ ID NO: 3 and an antisense primer consisting of an oligonucleotide complementary to an oligonucleotide of at least any 16 consecutive bases between nucleotides at positions 751 to 2460 in SEQ ID NO: 3;

a primer set of a sense primer consisting of at least any 16 consecutive bases between nucleotides at positions 1 to 750 in SEQ ID NO: 5 and an antisense primer consisting of an oligonucleotide complementary to an oligonucleotide of at least any 16 consecutive bases between nucleotides at positions 751 to 2088 in SEQ ID NO: 5; or a primer set of a sense primer consisting of at least any 16 consecutive bases between nucleotides at positions 1 to 750 in SEQ ID NO: 7 and an antisense primer consisting of an oligonucleotide complementary to an oligonucleotide of at least any 16 consecutive bases between nucleotides at positions 751 to 1923 in SEQ ID NO: 7.

Preferably, the distance between the positions selected for the sense primer and the antisense primer in the primer set is 1 kb or shorter or the size of the nucleic acid fragment to be amplified with the sense primer and the antisense primer is 1 kb or smaller since the efficiency of amplification becomes lower when the size of the nucleic acid fragment to be amplified is large. Moreover, the primers according to the present invention usually have a chain length of at least 15 bases, preferably at least 16 bases, and more preferably at least 18 bases. In one embodiment, the primers have a chain length of 15 to 40 bases, preferably 16 to 24 bases, and more preferably 18 to 24 bases.

The primers included in the primer set according to the present invention are not particularly limited, but, for example, they may be prepared by a chemical synthesis process.

The probes according to the present invention and the probes included in the probe set according to the present invention comprise an oligonucleotide that hybridizes with the polynucleotide and the complementary strand to the polynucleotide to be detected under stringent conditions (preferably under highly stringent conditions). The chain length of the probes according to the present invention and the probes included in the probe set according to the present invention may be selected according to the hybridization method to be used as appropriate by a person skilled in the art, but the probes preferably have a chain length of at least 16 bases.

In one embodiment, the probes according to the present invention comprise an oligonucleotide of at least 16 bases each in the upstream and downstream of the fusion point in the polynucleotide to be detected (for specific examples, a sequence of nucleotides at positions 735 to 766 in SEQ ID NO: 1, 3, 5, or 7) or an oligonucleotide complementary thereto.

In one embodiment, the probe set according to the present invention is a probe set comprising a probe designed for a part encoding CLDN18 (for example, any part in the CLDN18 gene region in the fusion polynucleotide) and a probe designed for a part encoding ARHGAP6 or a part encoding ARHGAP26 (for example, any part in the ARHGAP6 gene or ARHGAP26 gene region in the fusion polynucleotide).

In one embodiment, the probe set according to the present invention comprises a plurality of probes designed for a part encoding CLDN18 and a plurality of probes designed for a part encoding ARHGAP6 or a part encoding ARHGAP26.

In one embodiment, the probe set according to the present invention comprises the following:

a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 1 to 750 in SEQ ID NO: 1 and a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 751 to 3087 in SEQ ID NO: 1;

a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 1 to 750 in SEQ ID NO: 3 and a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 751 to 2460 in SEQ ID NO: 3;

a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 1 to 750 in SEQ ID NO: 5 and a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 751 to 2088 in SEQ ID NO: 5; or a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 1 to 750 in SEQ ID NO: 7 and a plurality of flanking probe pairs (preferably 10 to 25, more preferably 18 to 22, and more preferably 20 probe pairs) comprising an oligonucleotide complementary to an oligonucleotide of at least any 16 (preferably 16 to 30 bases, more preferably 18 to 25 bases) consecutive bases of nucleotides at positions 751 to 1923 in SEQ ID NO: 7.

The probes according to the present invention and the probes included in the probe set according to the present invention are not particularly limited, but, for example, they may be prepared by a chemical synthesis process.

The present invention comprises a kit for detection comprising a primer set according to the present invention, a probe according to the present invention, or a probe set according to the present invention. The kit for detection according to the present invention may comprise, in addition to the primer set according to the present invention, the probe according to the present invention, or the probe set according to the present invention, a component to be used with the primer set, probe, or probe set for detecting the polynucleotide to be detected, such as a reagent for amplifying a signal of the hybridization.

The present invention also comprises a kit for detection for detecting a polypeptide to be detected. Preferably, the kit for detection comprises an antibody (primary antibody) that recognizes a part derived from CLDN18 gene in the polypeptide to be detected and an antibody (primary antibody) that recognizes a part derived from ARHGAP6 gene or a part derived from ARHGAP26 gene in the polypeptide to be detected. More preferably, the kit may comprise oligonucleotide-conjugated secondary antibodies that respectively bind to the primary antibodies, 2 oligonucleotides partially complementary to the oligonucleotides conjugated to the secondary antibodies, a ligase capable of ligating the 2 oligonucleotides when they are in the vicinity to form a ring structure, a polymerase capable of extending a nucleic acid along the ring structure, and a labelled oligonucleotide probe.

The primer set, probe, probe set, and kit for detection according to the present invention may be used in the method for selection and the method for identifying a patient according to the present invention. In one embodiment, in relation to the primer set, probe, probe set, and kit for detection according to the present invention, a subject is a subject suspected to have pancreatic cancer or a subject having pancreatic cancer.

EXAMPLES

Unless otherwise specified, the present invention can be performed according to known methods. Further, the present invention can be performed, when using commercially available reagents, kits, or the like, according to instructions or protocols of the commercially available products.

Figure 2:
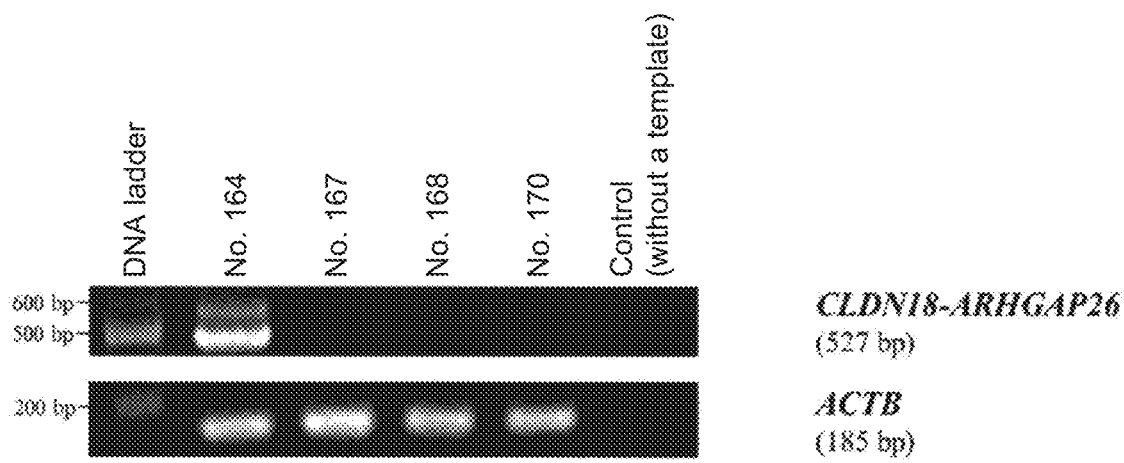
FIG. 2 shows the result of electrophoresis of PCR products which were amplified the region containing a fusion point of CLDN18-ARHGAP26 fusion gene by PCR from cDNA, as a template, prepared from total RNA purified from ascites of pancreatic cancer patients.

[Example 1] Detection of Polynucleotides Containing a Fusion Point of CLDN18-ARHGAP6/26 Fusion Gene The ascites collected from 26 pancreatic cancer patients in National Cancer Center Hospital and Kanamecho Hospital under the comprehensive consent were suspended in ISOGEN (NIPPON GENE CO., LTD.) according to the standard protocol of the reagent, and stored. From the conserved solution, total RNA was purified. Thereafter, reverse transcription reaction was performed with a High-Capacity cDNA Reverse Transcription Kit (Thermo Fisher Scientific K.K.) using 1 µg of the total RNA as a template according to the standard protocol of the reagent to synthesize cDNA. Next, PCR reaction (2 minutes at 94° C. followed by 15 seconds at 94° C., 15 seconds at 55° C. and 1 minute at 68° C., 30 or 35 cycles) was performed with DNA polymerase (AccuPrime™ Taq DNA Polymerase; Thermo Fisher Scientific K.K.) using the cDNA as a template (100 ng in terms of total RNA) with a reaction volume of 20 µL to amplify a region containing fusion point of the fusion gene. In this PCR, CLD-ARH_C6A12_partial fwd01 set forth in SEQ ID NO: 9, and CLDN18-ARHGAP6_CDS_R893 set forth in SEQ ID NO: 10 were used as primers for the amplification of CLDN18-ARHGAP6. Meanwhile, CLD-ARH_C6A12_partial fwd01 described above and CLD-ARH_C6A12_partial rev01 set forth in SEQ ID NO: 11 were used as primers for the amplification of CLDN18-ARHGAP26. Thereafter, nested PCR reaction was performed using 2 µL of the obtained PCR products as a template under the same conditions as described above. In this nested PCR, CLD-ARHC6A12_partial fwd02 set forth in SEQ ID NO: 12 and CLDN18-ARHGAP6 CDS_R815 set forth in SEQ ID NO: 13 were used as primers for the amplification of CLDN18-ARHGAP6. Meanwhile, CLD-ARH_C6A12_partial fwd02 described above and CLD-ARH_C6A12_partial rev02 set forth in SEQ ID NO: 14 were used as primers for the amplification of CLDN18-ARHGAP26. It is expected that the use of these primers yield PCR products having nucleotide length of about 300 bp when CLDN18-ARHGAP6 fusion genes exist, and PCR products having a nucleotide length of about 500 bp when CLDN18-ARHGAP26 fusion genes exist, respectively. Further, to confirm that the amount of template cDNA is the same level, PCR reaction (2 minutes at 94° C. followed by 15 seconds at 94° C., 15 seconds at 55° C. and 1 minute at 68° C., 25 cycles was performed for ACTB (β-actin) using ACTB_F2 set forth in SEQ ID NO: 15 and ACTB R2 set forth in SEQ ID NO: 16 as primers, and the same DNA polymerase as described above. Thereafter, the obtained PCR products were subjected to electrophoresis in 2% agarose gel (Lonza Ltd.). From the result of electrophoresis, PCR products having almost the same nucleotide length as described above was confirmed for CLDN18-ARHGAP6 in all of the 9 specimens (among the 9 specimens, 1 specimen (No. 193) is shown in FIG. 1). PCR products having almost the same nucleotide length as described above was also confirmed for CLDN18-ARHGAP26 in 1 specimen (No. 164) (FIG. 2).

Next, the PCR products of all the specimens of which the amplification product in the PCR reaction had been confirmed were cloned to cloning vectors (TOPO TA Cloning® Kit; Thermo Fisher Scientific K.K.). Sequence of the inserted nucleotides were determined using DNA sequencing service provided by Eurofins Genomics K.K. From the result, it was confirmed with respect to CLDN18-ARHGAP6 that the existence of the transcripts in all of the 9 specimens in which the amplification product had been confirmed, in which a nucleotide at position 803 in CLDN18 (NCBI accession number: NM_001002026.2) and a nucleotide at position 1462 in ARHGAP6 (NCBI accession number: NM_013427.2 or NCBI accession number: NM_006125.2) were fused, which had already been reported in gastric cancer. FIG. 3 shows the sequence of total 80 nucleotides, each 40 nucleotides upstream and downstream of the fusion point. It was also confirmed with respect to CLDN18-ARHGAP26 that the existence of the transcripts in one specimen in which the amplification products had been confirmed, in which a nucleotide at position 803 in CLDN18 (NCBI accession number: NM_001002026.2) and a nucleotide at position 1143 in ARHGAP26 (NCBI accession number: NM_015071.4 or NCBI accession number: NM_001135608.1) were fused. FIG. 3 shows the sequence of total 80 nucleotides, each 40 nucleotides upstream and downstream of the fusion point. From the results, it was showed that CLDN18-ARHGAP6/26 fusion genes are present not only in gastric cancer where the fusion gene has already been reported, but also in pancreatic cancer.

[Reference Example 1] Detection of CLDN18-ARHGAP26 Fusion Gene in an Established Cell Line Total RNA were prepared from total four cell lines: a gastric cancer cell line NSC-47C established by Department of Biomarker Discovery of National Cancer Center Research Institute in Japan; a gastric cancer cell line HSC-39 (obtained from Department of Animal Experimentation of National Cancer Center Research Institute in Japan); a gastric cancer cell line KATO-III (JCRB0611, JCRB Cell Bank); and a gastric cancer cell line NSC-9C established by Biomarker Discovery Department of National Cancer Center Japan Research Institute. For these total RNAs, reverse transcription was performed to synthesize cDNA using SuperScript® III First-Strand Synthesis System (Thermo Fisher Scientific K.K.), in which reverse transcriptase was included, and oligo (dT) primers (oligo(dT) 20 primer; Thermo Fisher Scientific K.K.) according to the standard protocols of the reagent.

Figure 4:
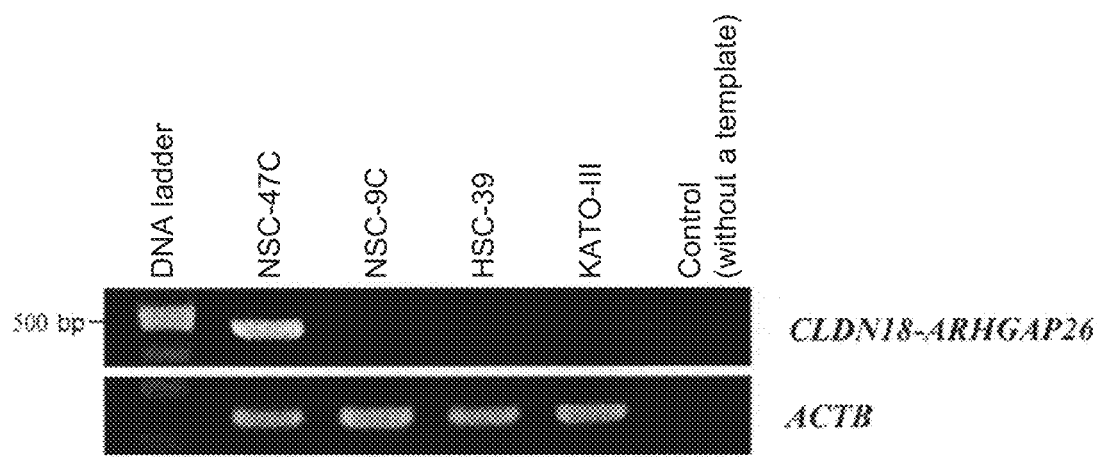
FIG. 4 shows the result of electrophoresis of PCR products which were amplified the region containing a fusion point of CLDN18-ARHGAP26 fusion gene by PCR from cDNA, as a template, prepared from a gastric cancer cell line NSC-47C.

Next, using the obtained cDNA as a template (200 ng in terms of total RNA), PCR reaction (2 minutes at 94° C. followed by 15 seconds at 94° C. 15 seconds at 55° C. and 1 minute at 68° C. 30 cycles) was performed using CLD-ARH_C6A12_partial fwd02 set forth in SEQ ID NO: 12 and CLD-ARH_C6A12_partial rev02 set forth in SEQ ID NO: 14, which were used in Example 1, as primers, and DNA polymerase (AccuPrime™ Taq DNA Polymerase; Thermo Fisher Scientific K.K.). After the PCR reaction, the obtained PCR products were subjected to electrophoresis in 2% agarose gel (Lonza Ltd.). From the results, it was confirmed that PCR products at the near the expected molecular weight (about 500 bp) was yielded only in the gastric cancer cell line NSC-47C (FIG. 4). Meanwhile, to confirm that the amount of the template cDNA was the same level, PCR reaction (2 minutes at 94° C. followed by 15 seconds at 94° C., 15 seconds at 55° C. and 1 minute at 68° C. 25 cycles was performed for ACTB (β-actin) using ACTB_F2 set forth in SEQ ID NO: 15 and ACTB R2 set forth in SEQ ID NO: 16 as primers and DNA polymerase as described above. From the results, tt was shown that the gastric cancer cell line NSC-47C expressed CLDN18-ARHGAP26 endogenously.

[Reference Example 2] Evaluation of Suppressive Effect of siRNA to CLDN18-ARHGAP26 Fusion Protein in a Gastric Cancer Cell Line Expressing CLDN18-ARHGAP26 Fusion Gene, and Evaluation of the Viability of the Cell Line Under the Same Condition The gastric cancer cell line NSC-47C that endogenously expresses CLDN18-ARHGAP26 fusion genes as shown in Reference Example 1 was cultured in a RPMI-1640 medium (Wako Pure Chemical Industries, Ltd.) containing 10% fetal bovine serum (Thermo Fisher Scientific K.K.), and then intended siRNA molecules were introduced into the cultured cells according to the standard protocol of Dharma-FECT™1, a gene transfection reagent (GE HealthCare, Inc.) (herein also referred to as "siRNA treatment"). More specifically, the gastric cancer cells were seeded into 6-well plates (140675, Nunc) at $2 \times 10^5$ cells per well, and then siRNAs targeting CLDN18 (s27688, Thermo Fisher Scientific K.K.), siRNAs targeting ARHGAP26 (s23013 and s23015, Thermo Fisher Scientific K.K.), and control siRNAs (AM4611, Thermo Fisher Scientific K.K.) were added onto the cells respectively so as to be 75 pmol (final concentration of 75 nM) and then cultured at 37° C. under 5% $CO_2$ condition for 72 hours. Among the siRNAs targeting ARHGAP26, s23013 is expected to target wild-type genes and also the fusion genes, while s23015 is expected to target only wild-type and not the fusion genes from their sequences. Furthermore, the siRNAs targeting CLDN18 is expected to target wild-type genes and also the fusion genes from the sequence. Hereinafter, the group treated with control siRNAs is referred to as Control siRNA group, the group treated with the siRNA targeting CLDN18 is referred to as CLDN18 siRNA group, and the group treated with s23013, one of siRNAs targeting ARHGAP26, is referred to as ARHGAP26 siRNA (Wild & Fusion) group, and the group treated with s23015, the other siRNA targeting ARHGAP26, is referred to as ARHGAP26 siRNA (Wild) group, respectively.

Figure 5:
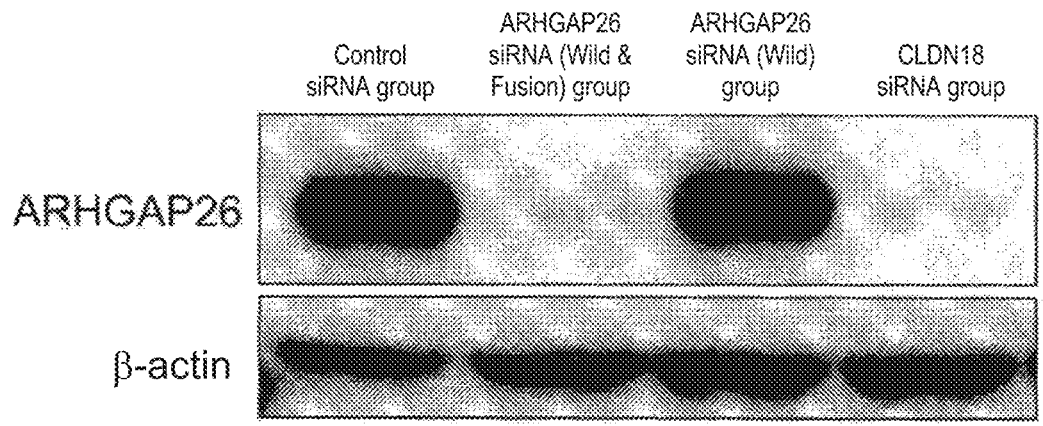
FIG. 5 shows the result of western blotting, confirming that the expression of CLDN18-ARHGAP26 fusion proteins were suppressed in a CLDN18 siRNA group and an ARHGAP26 siRNA (Wild & Fusion) group.

Suppressive effect by introducing siRNAs to the expression level of CLDN18-ARHGAP26 fusion protein was evaluated by Western blotting. Specifically, cell pellets after the culture were washed with PBS, lysed with 120 μL of Cell Lysis Buffer supplied in RhoA Pull-down Activation Assay Biochem Kit™ (Cytoskeleton, Inc.), and centrifuged at 4° C., 10000×g for 1 minute to collect supernatants. The supernatants were used as a protein extract. The protein concentration of this protein extract was measured by Protein Quantification Assay (MACHEREY-NAGEL GmbH & Co. KG). Thereafter, ARHGAP26 was detected by the following experiment. Specifically, the protein extract was loaded onto Novex™ WedgeWell™ 4-20% Tris-Glycine Gel (Thermo Fisher Scientific K.K.) at 20 μg per lane, and subjected to gel electrophoresis at 225 V for 25 minutes, then transferred to a PVDF membrane (Merck KGaA) using Trans-Blot® Turbo™ Blotting System (Bio-Rad Laboratories, Inc.) according to the standard protocol. After the transfer, the membrane was blocked with PBS containing 5% of ECL Blocking Agent (GE HealthCare, Inc.) (hereinafter, referred to as a blocking buffer) at room temperature for two hours. Then, the membrane was shaken in a primary antibody solution prepared by diluting anti ARHGAP26 antibody (HPA035107, Sigma-Aldrich Co. LLC) with the blocking buffer at a ratio of 1:500, and incubated at 4° C., overnight. After washing with PBS containing 0.05% Tween® 20 (Wako Pure Chemical Industries, Ltd.) (hereinafter, referred to as a washing buffer), the membrane was shaken in a secondary antibody solution prepared by diluting HRP-labeled anti-rabbit antibody (P0399, Dako) with the blocking buffer at a ratio of 1:3000, and incubated at room temperature for one hour. After washing with the washing buffer, Pierce Western Blotting Substrate Plus (Thermo Fisher Scientific K.K.) was added onto the membrane, and chemiluminescence signal on the membrane was detected using ImageQuant™ LAS 4000 mini (GE HealthCare, Inc.) ("detection of ARHGAP26"). For detection of β-actin, the membrane after the detection of ARHGAP26 was incubated with 14 mL of Restore™ PLUS Western Blot Stripping Buffer (Thermo Fisher Scientific K.K.) at room temperature for 15 minutes, washed with the washing buffer, and subjected to the same experimental procedure as described above. The antibody used in this experiment was an anti-β-actin antibody (4967, Cell Signaling Technology, Inc.), and the dilution ratio was 1:3000. As the result of Western blot, it was confirmed that the expression level of CLDN18-ARHGAP26 fusion protein was suppressed in the CLDN18 siRNA group and the ARHGAP26 siRNA (Wild & Fusion) group (FIG. 5).

Next, in order to evaluate the effect of CLDN18-ARHGAP26 fusion gene on the viability of cancer cells, siRNA treatment was performed to the gastric cancer cell line NSC-47C under the same conditions as described above. After 24 hours, medium was exchanged to RPMI-1640 medium containing 10% fetal bovine serum, and then 100 μL from each group were seeded respectively into 3 wells of a 96-well plate (167008, Nunc) so as to be 1000 cells per well. Wells only added RPMI-1640 medium containing 10% fetal bovine serum without cells were also prepared as a control (hereinafter, referred to as a medium group). Total three plates were prepared. The number of viable cells was measured at the day of cell seeding (referred to as day 1), at the additional 48 hours (referred to as day 3) and 120 hours (referred to as day 6) cultured at 37° C. under 5% $CO_2$ condition, respectively. The number of viable cells was determined by measuring luminescence intensity using Synergy™ H1 microplate reader (Biotech) with the same settings of the parameters following the standard protocol of CellTiter-Glo® 3D Cell Viability Assay (Promega Corporation). The viability in each siRNA group was calculated from a value obtained by subtracting the luminescence intensity of the medium group from the intensity in each siRNA group (hereinafter, referred to as correction value), where the correction value of day 1 in each siRNA group was determined as 1. The standard deviation was used as an error range. The student's t-test (two-sided test) was used f for the significance test, and it was determined significant when p<0.01.

As a result, it was found that, in the gastric cancer cell line NSC-47C which expresses CLDN18-ARHGAP26 fusion genes endogenously, the viability of the cells were attenuated significantly by suppressing the expression of CLDN18-ARHGAP26 fusion proteins (FIG. 6). Therefore, it was revealed that the suppression of the expression level of CLDN18-ARHGAP26 fusion genes in cancer cells that endogenously express the fusion genes inhibits the proliferation and/or attenuates the viability of the cancer cells.

From the above, it was revealed that CLDN18-ARHGAP26 is involved in tumor promoting ability. Meanwhile, it is expected that CLDN18-ARHGAP6 also relates to the tumor promoting ability, because ARHGAP6 is known to have the same function (enhancement of GTP hydrolase activity of RhoA) as ARHGAP26, and the ARHGAP6-derived sequence constituting the CLDN18-ARHGAP6 fusion gene also retains the Rho-GAP domain responsible for enhancing the function of GTP hydrolase activity same as the ARHGAP26-derived sequence constituting the CLDN18-ARHGAP26 fusion genes.

INDUSTRIAL APPLICABILITY

The method according to the present invention is for selecting subjects positive for the fusion genes of CLDN18 gene and ARHGAP6 gene, or subjects positive for the fusion genes of CLDN18 gene and ARHGAP26 gene, and the method is expected to be useful to identify subjects to be eligible for therapies with drugs. Moreover, the primer set, the probe, the probe set, and the kit for the detection according to the present invention can be used in the method according to the present invention.

The invention claimed is:

1. A method for detecting a fusion gene of a Claudin-18 (CLDN18) gene and a Rho GTPase Activating Protein 26 (ARHGAP26) gene, comprising detecting the presence of a polynucleotide encoding a fusion protein of CLDN18 and ARHGAP26 comprising an amino acid sequence having 90% or more identity with SEQ ID NO: 6 or SEQ ID NO: 8 in a sample obtained from a subject suspected to have pancreatic cancer or a subject having pancreatic cancer, wherein detecting comprises amplifying the polynucleotide in the sample, if present, using a primer set comprising a first primer corresponding to a section of the CLDN18 gene and a second primer corresponding to a section of the ARHGAP26 gene.

2. The method according to claim 1, wherein the polynucleotide encodes a polypeptide comprising SEQ ID NO: 6 or SEQ ID NO: 8.

3. The method according to claim 2, wherein the polynucleotide encodes a polypeptide consisting of SEQ ID NO 6 or SEQ ID NO: 8.

4. The method according to claim 1, wherein the polynucleotide is:
   a polynucleotide comprising a nucleotide sequence having 90% or more identity with SEQ ID NO: 17; or
   a polynucleotide comprising a nucleotide sequence of SEQ ID NO: 17.

5. The method according to claim 4, wherein the polynucleotide comprises SEQ ID NO: 17.

6. The method according to claim 1, wherein the method comprises hybridizing a probe to the polynucleotide.

7. The method according to claim 1, wherein the first primer is a sense primer and the second primer is an antisense primer, and wherein the antisense primer consists of an oligonucleotide that hybridizes with the polynucleotide under stringent conditions and the sense primer consists of an oligonucleotide that hybridizes with a complementary strand to the polynucleotide under stringent conditions.

8. The method according to claim 1, wherein the sample is body fluid or body cavity lavage fluid.

9. The method according to claim 1, wherein the sample is ascites or peritoneal cavity lavage fluid.

* * * * *

SEQUENCE LISTING

```
<160> NUMBER OF SEQ ID NOS: 21

<210> SEQ ID NO 1
<211> LENGTH: 3087
<212> TYPE: DNA
<213> ORGANISM: Homo sapience
<220> FEATURE:
<221> NAME/KEY: CDS
<222> LOCATION: (1)..(3084)

<400> SEQUENCE: 1 atg gcc gtg act gcc tgt cag ggc ttg ggg ttc gtg gtt tca ctg att        48
Met Ala Val Thr Ala Cys Gln Gly Leu Gly Phe Val Val Ser Leu Ile
1               5                   10                  15 ggg att gcg ggc atc att gct gcc acc tgc atg gac cag tgg agc acc        96
Gly Ile Ala Gly Ile Ile Ala Ala Thr Cys Met Asp Gln Trp Ser Thr
            20                  25                  30 caa gac ttg tac aac aac ccc gta aca gct gtt ttc aac tac cag ggg       144
Gln Asp Leu Tyr Asn Asn Pro Val Thr Ala Val Phe Asn Tyr Gln Gly
        35                  40                  45 ctg tgg cgc tcc tgt gtc cga gag agc tct ggc ttc acc gag tgc cgg       192
Leu Trp Arg Ser Cys Val Arg Glu Ser Ser Gly Phe Thr Glu Cys Arg
    50                  55                  60 ggc tac ttc acc ctg ctg ggg ctg cca gcc atg ctg cag gca gtg cga       240
Gly Tyr Phe Thr Leu Leu Gly Leu Pro Ala Met Leu Gln Ala Val Arg
65                  70                  75                  80 gcc ctg atg atc gta ggc atc gtc ctg ggt gcc att ggc ctc ctg gta       288
Ala Leu Met Ile Val Gly Ile Val Leu Gly Ala Ile Gly Leu Leu Val
                85                  90                  95 tcc atc ttt gcc ctg aaa tgc atc cgc att ggc agc atg gag gac tct       336
Ser Ile Phe Ala Leu Lys Cys Ile Arg Ile Gly Ser Met Glu Asp Ser
            100                 105                 110 gcc aaa gcc aac atg aca ctg acc tcc ggg atc atg ttc att gtc tca       384
Ala Lys Ala Asn Met Thr Leu Thr Ser Gly Ile Met Phe Ile Val Ser
        115                 120                 125 ggt ctt tgt gca att gct gga gtg tct gtg ttt gcc aac atg ctg gtg       432
Gly Leu Cys Ala Ile Ala Gly Val Ser Val Phe Ala Asn Met Leu Val
    130                 135                 140 act aac ttc tgg atg tcc aca gct aac atg tac acc ggc atg ggt ggg       480
Thr Asn Phe Trp Met Ser Thr Ala Asn Met Tyr Thr Gly Met Gly Gly
145                 150                 155                 160
```

```
atg gtg cag act gtt cag acc agg tac aca ttt ggt gcg gct ctg ttc     528
Met Val Gln Thr Val Gln Thr Arg Tyr Thr Phe Gly Ala Ala Leu Phe
            165                 170                 175 gtg ggc tgg gtc gct gga ggc ctc aca cta att ggg ggt gtg atg atg     576
Val Gly Trp Val Ala Gly Gly Leu Thr Leu Ile Gly Gly Val Met Met
        180                 185                 190 tgc atc gcc tgc cgg ggc ctg gca cca gaa gaa acc aac tac aaa gcc     624
Cys Ile Ala Cys Arg Gly Leu Ala Pro Glu Glu Thr Asn Tyr Lys Ala
            195                 200                 205 gtt tct tat cat gcc tca ggc cac agt gtt gcc tac aag cct gga ggc     672
Val Ser Tyr His Ala Ser Gly His Ser Val Ala Tyr Lys Pro Gly Gly
        210                 215                 220 ttc aag gcc agc act ggc ttt ggg tcc aac acc aaa aac aag aag ata     720
Phe Lys Ala Ser Thr Gly Phe Gly Ser Asn Thr Lys Asn Lys Lys Ile
225                 230                 235                 240 tac gat gga ggt gcc cgc aca gag gac gag ggt gat ttc acc tgg aac     768
Tyr Asp Gly Gly Ala Arg Thr Glu Asp Glu Gly Asp Phe Thr Trp Asn
            245                 250                 255 agc atg tca ggc cgc agt gta cgg ctg agg tca gtc ccc atc cag agt     816
Ser Met Ser Gly Arg Ser Val Arg Leu Arg Ser Val Pro Ile Gln Ser
        260                 265                 270 ctc tca gag ctg gag agg gcc cgg ctg cag gaa gtg gct ttt tat cag     864
Leu Ser Glu Leu Glu Arg Ala Arg Leu Gln Glu Val Ala Phe Tyr Gln
        275                 280                 285 ttg caa cag gac tgt gac ctg agc tgt cag atc acc att ccc aaa gat     912
Leu Gln Gln Asp Cys Asp Leu Ser Cys Gln Ile Thr Ile Pro Lys Asp
        290                 295                 300 gga caa aag aga aag aaa tct tta aga aag aaa ctg gat tca cta gga     960
Gly Gln Lys Arg Lys Lys Ser Leu Arg Lys Lys Leu Asp Ser Leu Gly
305                 310                 315                 320 aag gag aaa aac aaa gac aaa gaa ttc atc cca cag gca ttt gga atg    1008
Lys Glu Lys Asn Lys Asp Lys Glu Phe Ile Pro Gln Ala Phe Gly Met
            325                 330                 335 ccc tta tcc caa gtc att gcg aat gac agg gcc tat aaa ctc aag cag    1056
Pro Leu Ser Gln Val Ile Ala Asn Asp Arg Ala Tyr Lys Leu Lys Gln
        340                 345                 350 gac ttg cag agg gac gag cag aaa gat gca tct gac ttt gtg gct tcc    1104
Asp Leu Gln Arg Asp Glu Gln Lys Asp Ala Ser Asp Phe Val Ala Ser
        355                 360                 365 ctc ctc cca ttt gga aat aaa aga caa aac aaa gaa ctc tca agc agt    1152
Leu Leu Pro Phe Gly Asn Lys Arg Gln Asn Lys Glu Leu Ser Ser Ser
        370                 375                 380 aac tca tct ctc agc tca acc tca gaa aca ccg aat gag tca acg tcc    1200
Asn Ser Ser Leu Ser Ser Thr Ser Glu Thr Pro Asn Glu Ser Thr Ser
385                 390                 395                 400 cca aac acc ccg gaa ccg gct cct cgg gct agg agg agg ggt gcc atg    1248
Pro Asn Thr Pro Glu Pro Ala Pro Arg Ala Arg Arg Arg Gly Ala Met
            405                 410                 415 tca gtg gat tct atc acc gat ctt gat gac aat cag tct cga cta cta    1296
Ser Val Asp Ser Ile Thr Asp Leu Asp Asp Asn Gln Ser Arg Leu Leu
        420                 425                 430 gaa gct tta caa ctt tcc ttg cct gct gag gct caa agt aaa aag gaa    1344
Glu Ala Leu Gln Leu Ser Leu Pro Ala Glu Ala Gln Ser Lys Lys Glu
        435                 440                 445 aaa gcc aga gat aag aaa ctc agt ctg aat cct att tac aga cag gtc    1392
Lys Ala Arg Asp Lys Lys Leu Ser Leu Asn Pro Ile Tyr Arg Gln Val
450                 455                 460 cct agg ctg gtg gac agc tgc tgt cag cac cta gaa aaa cat ggc ctc    1440
Pro Arg Leu Val Asp Ser Cys Cys Gln His Leu Glu Lys His Gly Leu
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| 465   |       |       |       | 470   |       |       |       | 475   |       |       |       | 480   |       |       |       |      |
| cag   | aca   | gtg   | ggg   | ata   | ttc   | cga   | gtt   | gga   | agc   | tca   | aaa   | aag   | aga   | gtg   | aga   | 1488 |
| Gln   | Thr   | Val   | Gly   | Ile   | Phe   | Arg   | Val   | Gly   | Ser   | Ser   | Lys   | Lys   | Arg   | Val   | Arg   |      |
|       |       |       |       | 485   |       |       |       |       | 490   |       |       |       |       | 495   |       |      |
| caa   | tta   | cgt   | gag   | gaa   | ttt   | gac   | cgt   | ggg   | att   | gat   | gtc   | tct   | ctg   | gag   | gag   | 1536 |
| Gln   | Leu   | Arg   | Glu   | Glu   | Phe   | Asp   | Arg   | Gly   | Ile   | Asp   | Val   | Ser   | Leu   | Glu   | Glu   |      |
|       |       | 500   |       |       |       |       | 505   |       |       |       |       | 510   |       |       |       |      |
| gag   | cac   | agt   | gtt   | cat   | gat   | gtg   | gca   | gcc   | ttg   | ctg   | aaa   | gag   | ttc   | ctg   | agg   | 1584 |
| Glu   | His   | Ser   | Val   | His   | Asp   | Val   | Ala   | Ala   | Leu   | Leu   | Lys   | Glu   | Phe   | Leu   | Arg   |      |
|       |       | 515   |       |       |       | 520   |       |       |       |       | 525   |       |       |       |       |      |
| gac   | atg   | cca   | gac   | ccc   | ctt   | ctc   | acc   | agg   | gag   | ctg   | tac   | aca   | gct   | ttc   | atc   | 1632 |
| Asp   | Met   | Pro   | Asp   | Pro   | Leu   | Leu   | Thr   | Arg   | Glu   | Leu   | Tyr   | Thr   | Ala   | Phe   | Ile   |      |
|       | 530   |       |       |       |       | 535   |       |       |       |       | 540   |       |       |       |       |      |
| aac   | act   | ctc   | ttg   | ttg   | gag   | ccg   | gag   | gaa   | cag   | ctg   | ggc   | acc   | ttg   | cag   | ctc   | 1680 |
| Asn   | Thr   | Leu   | Leu   | Leu   | Glu   | Pro   | Glu   | Glu   | Gln   | Leu   | Gly   | Thr   | Leu   | Gln   | Leu   |      |
| 545   |       |       |       |       | 550   |       |       |       |       | 555   |       |       |       |       | 560   |      |
| ctc   | ata   | tac   | ctt   | cta   | cct   | ccc   | tgc   | aac   | tgc   | gac   | acc   | ctc   | cac   | cgc   | ctg   | 1728 |
| Leu   | Ile   | Tyr   | Leu   | Leu   | Pro   | Pro   | Cys   | Asn   | Cys   | Asp   | Thr   | Leu   | His   | Arg   | Leu   |      |
|       |       |       |       | 565   |       |       |       |       | 570   |       |       |       |       | 575   |       |      |
| cta   | cag   | ttc   | ctc   | tcc   | atc   | gtg   | gcc   | agg   | cat   | gcc   | gat   | gac   | aac   | atc   | agc   | 1776 |
| Leu   | Gln   | Phe   | Leu   | Ser   | Ile   | Val   | Ala   | Arg   | His   | Ala   | Asp   | Asp   | Asn   | Ile   | Ser   |      |
|       |       |       | 580   |       |       |       |       | 585   |       |       |       |       | 590   |       |       |      |
| aaa   | gat   | ggg   | caa   | gag   | gtc   | act   | ggg   | aat   | aaa   | atg   | aca   | tct   | cta   | aac   | tta   | 1824 |
| Lys   | Asp   | Gly   | Gln   | Glu   | Val   | Thr   | Gly   | Asn   | Lys   | Met   | Thr   | Ser   | Leu   | Asn   | Leu   |      |
|       |       | 595   |       |       |       |       | 600   |       |       |       |       | 605   |       |       |       |      |
| gcc   | acc   | ata   | ttt   | gga   | ccc   | aac   | ctg   | ctg   | cac   | aag   | cag   | aag   | tca   | tca   | gac   | 1872 |
| Ala   | Thr   | Ile   | Phe   | Gly   | Pro   | Asn   | Leu   | Leu   | His   | Lys   | Gln   | Lys   | Ser   | Ser   | Asp   |      |
|       | 610   |       |       |       |       | 615   |       |       |       |       | 620   |       |       |       |       |      |
| aaa   | gaa   | ttc   | tca   | gtt   | cag   | agt   | tca   | gcc   | cgg   | gct   | gag   | gag   | agc   | acg   | gcc   | 1920 |
| Lys   | Glu   | Phe   | Ser   | Val   | Gln   | Ser   | Ser   | Ala   | Arg   | Ala   | Glu   | Glu   | Ser   | Thr   | Ala   |      |
| 625   |       |       |       |       | 630   |       |       |       |       | 635   |       |       |       |       | 640   |      |
| atc   | atc   | gct   | gtt   | gtg   | caa   | aag   | atg   | att   | gaa   | aat   | tat   | gaa   | gcc   | ctg   | ttc   | 1968 |
| Ile   | Ile   | Ala   | Val   | Val   | Gln   | Lys   | Met   | Ile   | Glu   | Asn   | Tyr   | Glu   | Ala   | Leu   | Phe   |      |
|       |       |       |       | 645   |       |       |       |       | 650   |       |       |       |       | 655   |       |      |
| atg   | gtt   | ccc   | cca   | gat   | ctc   | cag   | aac   | gaa   | gtg   | ctg   | atc   | agc   | ctg   | tta   | gag   | 2016 |
| Met   | Val   | Pro   | Pro   | Asp   | Leu   | Gln   | Asn   | Glu   | Val   | Leu   | Ile   | Ser   | Leu   | Leu   | Glu   |      |
|       |       |       | 660   |       |       |       |       | 665   |       |       |       |       | 670   |       |       |      |
| acc   | gat   | cct   | gat   | gtc   | gtg   | gac   | tat   | tta   | ctc   | aga   | aga   | aag   | gct   | tcc   | caa   | 2064 |
| Thr   | Asp   | Pro   | Asp   | Val   | Val   | Asp   | Tyr   | Leu   | Leu   | Arg   | Arg   | Lys   | Ala   | Ser   | Gln   |      |
|       |       | 675   |       |       |       |       | 680   |       |       |       |       | 685   |       |       |       |      |
| tca   | tca   | agc   | cct   | gac   | atg   | ctg   | cag   | tcg   | gaa   | gtt   | tcc   | ttt   | tcc   | gtg   | gga   | 2112 |
| Ser   | Ser   | Ser   | Pro   | Asp   | Met   | Leu   | Gln   | Ser   | Glu   | Val   | Ser   | Phe   | Ser   | Val   | Gly   |      |
|       |       | 690   |       |       |       |       | 695   |       |       |       |       | 700   |       |       |       |      |
| ggg   | agg   | cat   | tca   | tct   | aca   | gac   | tcc   | aac   | aag   | gcc   | tcc   | agc   | gga   | gac   | atc   | 2160 |
| Gly   | Arg   | His   | Ser   | Ser   | Thr   | Asp   | Ser   | Asn   | Lys   | Ala   | Ser   | Ser   | Gly   | Asp   | Ile   |      |
| 705   |       |       |       |       | 710   |       |       |       |       | 715   |       |       |       |       | 720   |      |
| tcc   | cct   | tat   | gac   | aac   | aac   | tcc   | cca   | gtg   | ctg   | tct   | gag   | cgc   | tcc   | ctg   | ctg   | 2208 |
| Ser   | Pro   | Tyr   | Asp   | Asn   | Asn   | Ser   | Pro   | Val   | Leu   | Ser   | Glu   | Arg   | Ser   | Leu   | Leu   |      |
|       |       |       |       | 725   |       |       |       |       | 730   |       |       |       |       | 735   |       |      |
| gct   | atg   | caa   | gag   | gac   | gcg   | gcc   | ccg   | ggg   | ggc   | tcg   | gag   | aag   | ctt   | tac   | aga   | 2256 |
| Ala   | Met   | Gln   | Glu   | Asp   | Ala   | Ala   | Pro   | Gly   | Gly   | Ser   | Glu   | Lys   | Leu   | Tyr   | Arg   |      |
|       |       |       | 740   |       |       |       |       | 745   |       |       |       |       | 750   |       |       |      |
| gtg   | cca   | ggg   | cag   | ttt   | atg   | ctg   | gtg   | ggc   | cac   | ttg   | tcg   | tcg   | tca   | aag   | tca   | 2304 |
| Val   | Pro   | Gly   | Gln   | Phe   | Met   | Leu   | Val   | Gly   | His   | Leu   | Ser   | Ser   | Ser   | Lys   | Ser   |      |
|       |       |       | 755   |       |       |       |       | 760   |       |       |       |       | 765   |       |       |      |
| agg   | gaa   | agt   | tct   | cct   | gga   | cca   | agg   | ctt   | ggg   | aaa   | gat   | ctg   | tca   | gag   | gag   | 2352 |
| Arg   | Glu   | Ser   | Ser   | Pro   | Gly   | Pro   | Arg   | Leu   | Gly   | Lys   | Asp   | Leu   | Ser   | Glu   | Glu   |      |
|       |       | 770   |       |       |       |       | 775   |       |       |       |       | 780   |       |       |       |      |
| cct   | ttc   | gat   | atc   | tgg   | gga   | act   | tgg   | cat   | tca   | aca   | tta   | aaa   | agc   | gga   | tcc   | 2400 |

```
                 Pro Phe Asp Ile Trp Gly Thr Trp His Ser Thr Leu Lys Ser Gly Ser
                 785                 790                 795                 800 aaa gac cca gga atg aca ggt tcc tct gga gac att ttt gaa agc agc              2448
Lys Asp Pro Gly Met Thr Gly Ser Ser Gly Asp Ile Phe Glu Ser Ser
                 805                 810                 815 tcc cta aga gcg ggg ccc tgc tcc ctt tct caa ggg aac ctg tcc cca              2496
Ser Leu Arg Ala Gly Pro Cys Ser Leu Ser Gln Gly Asn Leu Ser Pro
                 820                 825                 830 aat tgg cct cgg tgg cag ggg agc ccc gca gag ctg gac agc gac acg              2544
Asn Trp Pro Arg Trp Gln Gly Ser Pro Ala Glu Leu Asp Ser Asp Thr
                 835                 840                 845 cag ggg gct cgg agg act cag gcc gca gcc ccc gcg acg gag ggc agg              2592
Gln Gly Ala Arg Arg Thr Gln Ala Ala Ala Pro Ala Thr Glu Gly Arg
                 850                 855                 860 gcc cac cct gcg gtg tcg cgc gcc tgc agc acg ccc cac gtc cag gtg              2640
Ala His Pro Ala Val Ser Arg Ala Cys Ser Thr Pro His Val Gln Val
865                 870                 875                 880 gca ggg aaa gcc gag cgg ccc acg gcc agg tcg gag cag tac ttg acc              2688
Ala Gly Lys Ala Glu Arg Pro Thr Ala Arg Ser Glu Gln Tyr Leu Thr
                885                 890                 895 ctg agc ggc gcc cac gac ctc agc gag agt gag ctg gat gtg gcc ggg              2736
Leu Ser Gly Ala His Asp Leu Ser Glu Ser Glu Leu Asp Val Ala Gly
            900                 905                 910 ctg cag agc cgg gcc aca cct cag tgc caa aga ccc cat ggg agt ggg              2784
Leu Gln Ser Arg Ala Thr Pro Gln Cys Gln Arg Pro His Gly Ser Gly
        915                 920                 925 agg gat gac aag cgg ccc ccg cct cca tac ccg ggc cca ggg aag ccc              2832
Arg Asp Asp Lys Arg Pro Pro Pro Pro Tyr Pro Gly Pro Gly Lys Pro
    930                 935                 940 gcg gca gcg gca gcc tgg atc cag ggg ccc ccg gaa ggc gtg gag aca              2880
Ala Ala Ala Ala Ala Trp Ile Gln Gly Pro Pro Glu Gly Val Glu Thr
945                 950                 955                 960 ccc acg gac cag gga ggc caa gca gcc gag cga gag cag cag gtc acg              2928
Pro Thr Asp Gln Gly Gly Gln Ala Ala Glu Arg Glu Gln Gln Val Thr
                965                 970                 975 cag aaa aaa ctg agc agc gcc aac tcc ctg cca gcg ggc gag cag gac              2976
Gln Lys Lys Leu Ser Ser Ala Asn Ser Leu Pro Ala Gly Glu Gln Asp
            980                 985                 990 agt ccg cgc ctg ggg gac gct ggc  tgg ctc gac tgg cag  aga gag cgc            3024
Ser Pro Arg Leu Gly Asp Ala Gly  Trp Leu Asp Trp Gln  Arg Glu Arg
        995                 1000                1005 tgg cag  atc tgg gag ctc ctg  tcg acc gac aac ccc  gat gcc ctg               3069
Trp Gln  Ile Trp Glu Leu Leu  Ser Thr Asp Asn Pro  Asp Ala Leu
    1010                1015                1020 ccc gag  acg ctg gtc tga                                                     3087
Pro Glu  Thr Leu Val
    1025
```

<210> SEQ ID NO 2
<211> LENGTH: 1028
<212> TYPE: PRT
<213> ORGANISM: Homo sapience

<400> SEQUENCE: 2

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45
```

```
Leu Trp Arg Ser Cys Val Arg Glu Ser Ser Gly Phe Thr Glu Cys Arg
     50                  55                  60

Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                 85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Gly Asp Phe Thr Trp Asn
                245                 250                 255

Ser Met Ser Gly Arg Ser Val Arg Leu Arg Ser Val Pro Ile Gln Ser
            260                 265                 270

Leu Ser Glu Leu Glu Arg Ala Arg Leu Gln Glu Val Ala Phe Tyr Gln
        275                 280                 285

Leu Gln Gln Asp Cys Asp Leu Ser Cys Gln Ile Thr Ile Pro Lys Asp
    290                 295                 300

Gly Gln Lys Arg Lys Ser Leu Arg Lys Leu Asp Ser Leu Gly
305                 310                 315                 320

Lys Glu Lys Asn Lys Asp Lys Glu Phe Ile Pro Gln Ala Phe Gly Met
                325                 330                 335

Pro Leu Ser Gln Val Ile Ala Asn Asp Arg Ala Tyr Lys Leu Lys Gln
            340                 345                 350

Asp Leu Gln Arg Asp Glu Gln Lys Asp Ala Ser Asp Phe Val Ala Ser
        355                 360                 365

Leu Leu Pro Phe Gly Asn Lys Arg Gln Asn Lys Glu Leu Ser Ser Ser
    370                 375                 380

Asn Ser Ser Leu Ser Ser Thr Ser Glu Thr Pro Asn Glu Ser Thr Ser
385                 390                 395                 400

Pro Asn Thr Pro Glu Pro Ala Pro Arg Ala Arg Arg Gly Ala Met
                405                 410                 415

Ser Val Asp Ser Ile Thr Asp Leu Asp Asp Asn Gln Ser Arg Leu Leu
            420                 425                 430

Glu Ala Leu Gln Leu Ser Leu Pro Ala Glu Ala Gln Ser Lys Lys Glu
        435                 440                 445

Lys Ala Arg Asp Lys Lys Leu Ser Leu Asn Pro Ile Tyr Arg Gln Val
450                 455                 460
```

```
Pro Arg Leu Val Asp Ser Cys Cys Gln His Leu Glu Lys His Gly Leu
465                 470                 475                 480

Gln Thr Val Gly Ile Phe Arg Val Gly Ser Lys Lys Arg Val Arg
            485                 490                 495

Gln Leu Arg Glu Glu Phe Asp Arg Gly Ile Asp Val Ser Leu Glu Glu
            500                 505                 510

Glu His Ser Val His Asp Val Ala Leu Leu Lys Glu Phe Leu Arg
        515                 520                 525

Asp Met Pro Asp Pro Leu Leu Thr Arg Glu Leu Tyr Thr Ala Phe Ile
    530                 535                 540

Asn Thr Leu Leu Leu Glu Pro Glu Gln Leu Gly Thr Leu Gln Leu
545                 550                 555                 560

Leu Ile Tyr Leu Leu Pro Pro Cys Asn Cys Asp Thr Leu His Arg Leu
            565                 570                 575

Leu Gln Phe Leu Ser Ile Val Ala Arg His Ala Asp Asp Asn Ile Ser
            580                 585                 590

Lys Asp Gly Gln Glu Val Thr Gly Asn Lys Met Thr Ser Leu Asn Leu
    595                 600                 605

Ala Thr Ile Phe Gly Pro Asn Leu Leu His Lys Gln Lys Ser Ser Asp
610                 615                 620

Lys Glu Phe Ser Val Gln Ser Ser Ala Arg Ala Glu Glu Ser Thr Ala
625                 630                 635                 640

Ile Ile Ala Val Val Gln Lys Met Ile Glu Asn Tyr Glu Ala Leu Phe
                645                 650                 655

Met Val Pro Pro Asp Leu Gln Asn Glu Val Leu Ile Ser Leu Leu Glu
        660                 665                 670

Thr Asp Pro Asp Val Val Asp Tyr Leu Leu Arg Arg Lys Ala Ser Gln
        675                 680                 685

Ser Ser Ser Pro Asp Met Leu Gln Ser Glu Val Ser Phe Ser Val Gly
        690                 695                 700

Gly Arg His Ser Ser Thr Asp Ser Asn Lys Ala Ser Ser Gly Asp Ile
705                 710                 715                 720

Ser Pro Tyr Asp Asn Asn Ser Pro Val Leu Ser Glu Arg Ser Leu Leu
            725                 730                 735

Ala Met Gln Glu Asp Ala Ala Pro Gly Gly Ser Glu Lys Leu Tyr Arg
            740                 745                 750

Val Pro Gly Gln Phe Met Leu Val Gly His Leu Ser Ser Ser Lys Ser
        755                 760                 765

Arg Glu Ser Ser Pro Gly Pro Arg Leu Gly Lys Asp Leu Ser Glu Glu
770                 775                 780

Pro Phe Asp Ile Trp Gly Thr Trp His Ser Thr Leu Lys Ser Gly Ser
785                 790                 795                 800

Lys Asp Pro Gly Met Thr Gly Ser Ser Gly Asp Ile Phe Glu Ser Ser
            805                 810                 815

Ser Leu Arg Ala Gly Pro Cys Ser Leu Ser Gln Gly Asn Leu Ser Pro
            820                 825                 830

Asn Trp Pro Arg Trp Gln Gly Ser Pro Ala Glu Leu Asp Ser Asp Thr
        835                 840                 845

Gln Gly Ala Arg Arg Thr Gln Ala Ala Pro Ala Thr Glu Gly Arg
        850                 855                 860

Ala His Pro Ala Val Ser Arg Ala Cys Ser Thr Pro His Val Gln Val
865                 870                 875                 880

Ala Gly Lys Ala Glu Arg Pro Thr Ala Arg Ser Glu Gln Tyr Leu Thr
```

```
                              885                 890                 895
Leu Ser Gly Ala His Asp Leu Ser Glu Ser Glu Leu Asp Val Ala Gly
            900                 905                 910

Leu Gln Ser Arg Ala Thr Pro Gln Cys Gln Arg Pro His Gly Ser Gly
            915                 920                 925

Arg Asp Asp Lys Arg Pro Pro Pro Tyr Pro Gly Pro Lys Pro
            930                 935                 940

Ala Ala Ala Ala Ala Trp Ile Gln Gly Pro Pro Glu Gly Val Glu Thr
945                 950                 955                 960

Pro Thr Asp Gln Gly Gly Gln Ala Ala Glu Arg Glu Gln Gln Val Thr
                965                 970                 975

Gln Lys Lys Leu Ser Ser Ala Asn Ser Leu Pro Ala Gly Glu Gln Asp
            980                 985                 990

Ser Pro Arg Leu Gly Asp Ala Gly  Trp Leu Asp Trp Gln  Arg Glu Arg
            995                 1000                1005

Trp Gln  Ile Trp Glu Leu Leu  Ser Thr Asp Asn Pro  Asp Ala Leu
    1010            1015                1020

Pro Glu  Thr Leu Val
    1025

<210> SEQ ID NO 3
<211> LENGTH: 2460
<212> TYPE: DNA
<213> ORGANISM: Homo sapience
<220> FEATURE:
<221> NAME/KEY: CDS
<222> LOCATION: (1)..(2457)

<400> SEQUENCE: 3 atg gcc gtg act gcc tgt cag ggc ttg ggg ttc gtg gtt tca ctg att        48
Met Ala Val Thr Ala Cys Gln Gly Leu Gly Phe Val Val Ser Leu Ile
1               5                   10                  15 ggg att gcg ggc atc att gct gcc acc tgc atg gac cag tgg agc acc        96
Gly Ile Ala Gly Ile Ile Ala Ala Thr Cys Met Asp Gln Trp Ser Thr
                20                  25                  30 caa gac ttg tac aac aac ccc gta aca gct gtt ttc aac tac cag ggg       144
Gln Asp Leu Tyr Asn Asn Pro Val Thr Ala Val Phe Asn Tyr Gln Gly
            35                  40                  45 ctg tgg cgc tcc tgt gtc cga gag agc tct ggc ttc acc gag tgc cgg       192
Leu Trp Arg Ser Cys Val Arg Glu Ser Ser Gly Phe Thr Glu Cys Arg
        50                  55                  60 ggc tac ttc acc ctg ctg ggg ctg cca gcc atg ctg cag gca gtg cga       240
Gly Tyr Phe Thr Leu Leu Gly Leu Pro Ala Met Leu Gln Ala Val Arg
65                  70                  75                  80 gcc ctg atg atc gta ggc atc gtc ctg ggt gcc att ggc ctc ctg gta       288
Ala Leu Met Ile Val Gly Ile Val Leu Gly Ala Ile Gly Leu Leu Val
                85                  90                  95 tcc atc ttt gcc ctg aaa tgc atc cgc att ggc agc atg gag gac tct       336
Ser Ile Phe Ala Leu Lys Cys Ile Arg Ile Gly Ser Met Glu Asp Ser
                100                 105                 110 gcc aaa gcc aac atg aca ctg acc tcc ggg atc atg ttc att gtc tca       384
Ala Lys Ala Asn Met Thr Leu Thr Ser Gly Ile Met Phe Ile Val Ser
            115                 120                 125 ggt ctt tgt gca att gct gga gtg tct gtg ttt gcc aac atg ctg gtg       432
Gly Leu Cys Ala Ile Ala Gly Val Ser Val Phe Ala Asn Met Leu Val
        130                 135                 140 act aac ttc tgg atg tcc aca gct aac atg tac acc ggc atg ggt ggg       480
Thr Asn Phe Trp Met Ser Thr Ala Asn Met Tyr Thr Gly Met Gly Gly
145                 150                 155                 160
```

```
atg gtg cag act gtt cag acc agg tac aca ttt ggt gcg gct ctg ttc    528
Met Val Gln Thr Val Gln Thr Arg Tyr Thr Phe Gly Ala Ala Leu Phe
            165                 170                 175 gtg ggc tgg gtc gct gga ggc ctc aca cta att ggg ggt gtg atg atg    576
Val Gly Trp Val Ala Gly Gly Leu Thr Leu Ile Gly Gly Val Met Met
        180                 185                 190 tgc atc gcc tgc cgg ggc ctg gca cca gaa gaa acc aac tac aaa gcc    624
Cys Ile Ala Cys Arg Gly Leu Ala Pro Glu Glu Thr Asn Tyr Lys Ala
            195                 200                 205 gtt tct tat cat gcc tca ggc cac agt gtt gcc tac aag cct gga ggc    672
Val Ser Tyr His Ala Ser Gly His Ser Val Ala Tyr Lys Pro Gly Gly
        210                 215                 220 ttc aag gcc agc act ggc ttt ggg tcc aac acc aaa aac aag aag ata    720
Phe Lys Ala Ser Thr Gly Phe Gly Ser Asn Thr Lys Asn Lys Lys Ile
225                 230                 235                 240 tac gat gga ggt gcc cgc aca gag gac gag ggt gat ttc acc tgg aac    768
Tyr Asp Gly Gly Ala Arg Thr Glu Asp Glu Gly Asp Phe Thr Trp Asn
                245                 250                 255 agc atg tca ggc cgc agt gta cgg ctg agg tca gtc ccc atc cag agt    816
Ser Met Ser Gly Arg Ser Val Arg Leu Arg Ser Val Pro Ile Gln Ser
            260                 265                 270 ctc tca gag ctg gag agg gcc cgg ctg cag gaa gtg gct ttt tat cag    864
Leu Ser Glu Leu Glu Arg Ala Arg Leu Gln Glu Val Ala Phe Tyr Gln
        275                 280                 285 ttg caa cag gac tgt gac ctg agc tgt cag atc acc att ccc aaa gat    912
Leu Gln Gln Asp Cys Asp Leu Ser Cys Gln Ile Thr Ile Pro Lys Asp
    290                 295                 300 gga caa aag aga aag aaa tct tta aga aag aaa ctg gat tca cta gga    960
Gly Gln Lys Arg Lys Lys Ser Leu Arg Lys Lys Leu Asp Ser Leu Gly
305                 310                 315                 320 aag gag aaa aac aaa gac aaa gaa ttc atc cca cag gca ttt gga atg   1008
Lys Glu Lys Asn Lys Asp Lys Glu Phe Ile Pro Gln Ala Phe Gly Met
                325                 330                 335 ccc tta tcc caa gtc att gcg aat gac agg gcc tat aaa ctc aag cag   1056
Pro Leu Ser Gln Val Ile Ala Asn Asp Arg Ala Tyr Lys Leu Lys Gln
            340                 345                 350 gac ttg cag agg gac gag cag aaa gat gca tct gac ttt gtg gct tcc   1104
Asp Leu Gln Arg Asp Glu Gln Lys Asp Ala Ser Asp Phe Val Ala Ser
        355                 360                 365 ctc ctc cca ttt gga aat aaa aga caa aac aaa gaa ctc tca agc agt   1152
Leu Leu Pro Phe Gly Asn Lys Arg Gln Asn Lys Glu Leu Ser Ser Ser
    370                 375                 380 aac tca tct ctc agc tca acc tca gaa aca ccg aat gag tca acg tcc   1200
Asn Ser Ser Leu Ser Ser Thr Ser Glu Thr Pro Asn Glu Ser Thr Ser
385                 390                 395                 400 cca aac acc ccg gaa ccg gct cct cgg gct agg agg agg ggt gcc atg   1248
Pro Asn Thr Pro Glu Pro Ala Pro Arg Ala Arg Arg Arg Gly Ala Met
                405                 410                 415 tca gtg gat tct atc acc gat ctt gat gac aat cag tct cga cta cta   1296
Ser Val Asp Ser Ile Thr Asp Leu Asp Asp Asn Gln Ser Arg Leu Leu
            420                 425                 430 gaa gct tta caa ctt tcc ttg cct gct gag gct caa agt aaa aag gaa   1344
Glu Ala Leu Gln Leu Ser Leu Pro Ala Glu Ala Gln Ser Lys Lys Glu
        435                 440                 445 aaa gcc aga gat aag aaa ctc agt ctg aat cct att tac aga cag gtc   1392
Lys Ala Arg Asp Lys Lys Leu Ser Leu Asn Pro Ile Tyr Arg Gln Val
    450                 455                 460 cct agg ctg gtg gac agc tgc tgt cag cac cta gaa aaa cat ggc ctc   1440
Pro Arg Leu Val Asp Ser Cys Cys Gln His Leu Glu Lys His Gly Leu
```

-continued

```
             465                 470                 475                 480
cag aca gtg ggg ata ttc cga gtt gga agc tca aaa aag aga gtg aga       1488
Gln Thr Val Gly Ile Phe Arg Val Gly Ser Ser Lys Lys Arg Val Arg
                    485                 490                 495 caa tta cgt gag gaa ttt gac cgt ggg att gat gtc tct ctg gag gag       1536
Gln Leu Arg Glu Glu Phe Asp Arg Gly Ile Asp Val Ser Leu Glu Glu
                500                 505                 510 gag cac agt gtt cat gat gtg gca gcc ttg ctg aaa gag ttc ctg agg       1584
Glu His Ser Val His Asp Val Ala Ala Leu Leu Lys Glu Phe Leu Arg
            515                 520                 525 gac atg cca gac ccc ctt ctc acc agg gag ctg tac aca gct ttc atc       1632
Asp Met Pro Asp Pro Leu Leu Thr Arg Glu Leu Tyr Thr Ala Phe Ile
        530                 535                 540 aac act ctc ttg ttg gag ccg gag gaa cag ctg ggc acc ttg cag ctc       1680
Asn Thr Leu Leu Leu Glu Pro Glu Glu Gln Leu Gly Thr Leu Gln Leu
545                 550                 555                 560 ctc ata tac ctt cta cct ccc tgc aac tgc gac acc ctc cac cgc ctg       1728
Leu Ile Tyr Leu Leu Pro Pro Cys Asn Cys Asp Thr Leu His Arg Leu
                    565                 570                 575 cta cag ttc ctc tcc atc gtg gcc agg cat gcc gat gac aac atc agc       1776
Leu Gln Phe Leu Ser Ile Val Ala Arg His Ala Asp Asp Asn Ile Ser
                580                 585                 590 aaa gat ggg caa gag gtc act ggg aat aaa atg aca tct cta aac tta       1824
Lys Asp Gly Gln Glu Val Thr Gly Asn Lys Met Thr Ser Leu Asn Leu
            595                 600                 605 gcc acc ata ttt gga ccc aac ctg ctg cac aag cag aag tca tca gac       1872
Ala Thr Ile Phe Gly Pro Asn Leu Leu His Lys Gln Lys Ser Ser Asp
        610                 615                 620 aaa gaa ttc tca gtt cag agt tca gcc cgg gct gag gag agc acg gcc       1920
Lys Glu Phe Ser Val Gln Ser Ser Ala Arg Ala Glu Glu Ser Thr Ala
625                 630                 635                 640 atc atc gct gtt gtg caa aag atg att gaa aat tat gaa gcc ctg ttc       1968
Ile Ile Ala Val Val Gln Lys Met Ile Glu Asn Tyr Glu Ala Leu Phe
                    645                 650                 655 atg gtt ccc cca gat ctc cag aac gaa gtg ctg atc agc ctg tta gag       2016
Met Val Pro Pro Asp Leu Gln Asn Glu Val Leu Ile Ser Leu Leu Glu
                660                 665                 670 acc gat cct gat gtc gtg gac tat tta ctc aga aga aag gct tcc caa       2064
Thr Asp Pro Asp Val Val Asp Tyr Leu Leu Arg Arg Lys Ala Ser Gln
            675                 680                 685 tca tca agc cct gac atg ctg cag tcg gaa gtt tcc ttt tcc gtg gga       2112
Ser Ser Ser Pro Asp Met Leu Gln Ser Glu Val Ser Phe Ser Val Gly
        690                 695                 700 ggg agg cat tca tct aca gac tcc aac aag gcc tcc agc gga gac atc       2160
Gly Arg His Ser Ser Thr Asp Ser Asn Lys Ala Ser Ser Gly Asp Ile
705                 710                 715                 720 tcc cct tat gac aac aac tcc cca gtg ctg tct gag cgc tcc ctg ctg       2208
Ser Pro Tyr Asp Asn Asn Ser Pro Val Leu Ser Glu Arg Ser Leu Leu
                    725                 730                 735 gct atg caa gag gac gcg gcc ccg ggg ggc tcg gag aag ctt tac aga       2256
Ala Met Gln Glu Asp Ala Ala Pro Gly Gly Ser Glu Lys Leu Tyr Arg
                740                 745                 750 gtg cca ggg cag ttt atg ctg gtg ggc cac ttg tcg tcg tca aag tca       2304
Val Pro Gly Gln Phe Met Leu Val Gly His Leu Ser Ser Ser Lys Ser
            755                 760                 765 agg gaa agt tct cct gga cca agg ctt ggg aaa ggt aac tgg agc ctg       2352
Arg Glu Ser Ser Pro Gly Pro Arg Leu Gly Lys Gly Asn Trp Ser Leu
        770                 775                 780 gcc agc agg cgc tgg cca aaa caa gcg acc ctc ctc ttg ttg cat gtg       2400
```

```
Ala Ser Arg Arg Trp Pro Lys Gln Ala Thr Leu Leu Leu His Val
            785             790                 795             800 gca tgg tgt ggg gct ctt cgg acc ttc tct tcg tct ctc cct tat ttg   2448
Ala Trp Cys Gly Ala Leu Arg Thr Phe Ser Ser Ser Leu Pro Tyr Leu
            805                 810                 815 atg ttt ctg taa                                                    2460
Met Phe Leu <210> SEQ ID NO 4
<211> LENGTH: 819
<212> TYPE: PRT
<213> ORGANISM: Homo sapience

<400> SEQUENCE: 4

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Gly Asp Phe Thr Trp Asn
                245                 250                 255

Ser Met Ser Gly Arg Ser Val Arg Leu Arg Ser Val Pro Ile Gln Ser
            260                 265                 270

Leu Ser Glu Leu Glu Arg Ala Arg Leu Gln Glu Val Ala Phe Tyr Gln
        275                 280                 285

Leu Gln Gln Asp Cys Asp Leu Ser Cys Gln Ile Thr Ile Pro Lys Asp
    290                 295                 300

Gly Gln Lys Arg Lys Lys Ser Leu Arg Lys Leu Asp Ser Leu Gly
305                 310                 315                 320

Lys Glu Lys Asn Lys Asp Lys Glu Phe Ile Pro Gln Ala Phe Gly Met
```

```
                   325                 330                 335
        Pro Leu Ser Gln Val Ile Ala Asn Asp Arg Ala Tyr Lys Leu Lys Gln
            340                 345                 350

Asp Leu Gln Arg Asp Glu Gln Lys Asp Ala Ser Asp Phe Val Ala Ser
            355                 360                 365

Leu Leu Pro Phe Gly Asn Lys Arg Gln Asn Lys Glu Leu Ser Ser Ser
            370                 375                 380

Asn Ser Ser Leu Ser Ser Thr Ser Glu Thr Pro Asn Glu Ser Thr Ser
        385                 390                 395                 400

Pro Asn Thr Pro Glu Pro Ala Pro Arg Ala Arg Arg Gly Ala Met
                            405                 410                 415

Ser Val Asp Ser Ile Thr Asp Leu Asp Asp Asn Gln Ser Arg Leu Leu
                            420                 425                 430

Glu Ala Leu Gln Leu Ser Leu Pro Ala Glu Ala Gln Ser Lys Lys Glu
                            435                 440                 445

Lys Ala Arg Asp Lys Lys Leu Ser Leu Asn Pro Ile Tyr Arg Gln Val
            450                 455                 460

Pro Arg Leu Val Asp Ser Cys Cys Gln His Leu Glu Lys His Gly Leu
        465                 470                 475                 480

Gln Thr Val Gly Ile Phe Arg Val Gly Ser Ser Lys Lys Arg Val Arg
                            485                 490                 495

Gln Leu Arg Glu Glu Phe Asp Arg Gly Ile Asp Val Ser Leu Glu Glu
                            500                 505                 510

Glu His Ser Val His Asp Val Ala Ala Leu Leu Lys Glu Phe Leu Arg
                            515                 520                 525

Asp Met Pro Asp Pro Leu Leu Thr Arg Glu Leu Tyr Thr Ala Phe Ile
            530                 535                 540

Asn Thr Leu Leu Leu Glu Pro Glu Gln Leu Gly Thr Leu Gln Leu
        545                 550                 555                 560

Leu Ile Tyr Leu Leu Pro Pro Cys Asn Cys Asp Thr Leu His Arg Leu
                            565                 570                 575

Leu Gln Phe Leu Ser Ile Val Ala Arg His Ala Asp Asp Asn Ile Ser
                            580                 585                 590

Lys Asp Gly Gln Glu Val Thr Gly Asn Lys Met Thr Ser Leu Asn Leu
                            595                 600                 605

Ala Thr Ile Phe Gly Pro Asn Leu Leu His Lys Gln Lys Ser Ser Asp
            610                 615                 620

Lys Glu Phe Ser Val Gln Ser Ser Ala Arg Ala Glu Glu Ser Thr Ala
        625                 630                 635                 640

Ile Ile Ala Val Val Gln Lys Met Ile Glu Asn Tyr Glu Ala Leu Phe
                            645                 650                 655

Met Val Pro Pro Asp Leu Gln Asn Glu Val Leu Ile Ser Leu Leu Glu
                            660                 665                 670

Thr Asp Pro Asp Val Val Asp Tyr Leu Leu Arg Arg Lys Ala Ser Gln
                            675                 680                 685

Ser Ser Ser Pro Asp Met Leu Gln Ser Glu Val Ser Phe Ser Val Gly
            690                 695                 700

Gly Arg His Ser Ser Thr Asp Ser Asn Lys Ala Ser Ser Gly Asp Ile
        705                 710                 715                 720

Ser Pro Tyr Asp Asn Asn Ser Pro Val Leu Ser Glu Arg Ser Leu Leu
                            725                 730                 735

Ala Met Gln Glu Asp Ala Ala Pro Gly Gly Ser Glu Lys Leu Tyr Arg
                            740                 745                 750
```

<210> SEQ ID NO 5
<211> LENGTH: 2088
<212> TYPE: DNA
<213> ORGANISM: Homo sapience
<220> FEATURE:
<221> NAME/KEY: CDS
<222> LOCATION: (1)..(2085)

<400> SEQUENCE: 5

| | | |
|---|---|---|
| atg gcc gtg act gcc tgt cag ggc ttg ggg ttc gtg gtt tca ctg att<br>Met Ala Val Thr Ala Cys Gln Gly Leu Gly Phe Val Val Ser Leu Ile<br>1                        5                       10                  15 | 48 |

```
atg gcc gtg act gcc tgt cag ggc ttg ggg ttc gtg gtt tca ctg att      48
Met Ala Val Thr Ala Cys Gln Gly Leu Gly Phe Val Val Ser Leu Ile
1               5                   10                  15 ggg att gcg ggc atc att gct gcc acc tgc atg gac cag tgg agc acc      96
Gly Ile Ala Gly Ile Ile Ala Ala Thr Cys Met Asp Gln Trp Ser Thr
            20                  25                  30 caa gac ttg tac aac aac ccc gta aca gct gtt ttc aac tac cag ggg     144
Gln Asp Leu Tyr Asn Asn Pro Val Thr Ala Val Phe Asn Tyr Gln Gly
        35                  40                  45 ctg tgg cgc tcc tgt gtc cga gag agc tct ggc ttc acc gag tgc cgg     192
Leu Trp Arg Ser Cys Val Arg Glu Ser Ser Gly Phe Thr Glu Cys Arg
50                  55                  60 ggc tac ttc acc ctg ctg ggg ctg cca gcc atg ctg cag gca gtg cga     240
Gly Tyr Phe Thr Leu Leu Gly Leu Pro Ala Met Leu Gln Ala Val Arg
65                  70                  75                  80 gcc ctg atg atc gta ggc atc gtc ctg ggt gcc att ggc ctc ctg gta     288
Ala Leu Met Ile Val Gly Ile Val Leu Gly Ala Ile Gly Leu Leu Val
                85                  90                  95 tcc atc ttt gcc ctg aaa tgc atc cgc att ggc agc atg gag gac tct     336
Ser Ile Phe Ala Leu Lys Cys Ile Arg Ile Gly Ser Met Glu Asp Ser
            100                 105                 110 gcc aaa gcc aac atg aca ctg acc tcc ggg atc atg ttc att gtc tca     384
Ala Lys Ala Asn Met Thr Leu Thr Ser Gly Ile Met Phe Ile Val Ser
        115                 120                 125 ggt ctt tgt gca att gct gga gtg tct gtg ttt gcc aac atg ctg gtg     432
Gly Leu Cys Ala Ile Ala Gly Val Ser Val Phe Ala Asn Met Leu Val
    130                 135                 140 act aac ttc tgg atg tcc aca gct aac atg tac acc ggc atg ggt ggg     480
Thr Asn Phe Trp Met Ser Thr Ala Asn Met Tyr Thr Gly Met Gly Gly
145                 150                 155                 160 atg gtg cag act gtt cag acc agg tac aca ttt ggt gcg gct ctg ttc     528
Met Val Gln Thr Val Gln Thr Arg Tyr Thr Phe Gly Ala Ala Leu Phe
                165                 170                 175 gtg ggc tgg gtc gct gga ggc ctc aca cta att ggg ggt gtg atg atg     576
Val Gly Trp Val Ala Gly Gly Leu Thr Leu Ile Gly Gly Val Met Met
            180                 185                 190 tgc atc gcc tgc cgg ggc ctg gca cca gaa gaa acc aac tac aaa gcc     624
Cys Ile Ala Cys Arg Gly Leu Ala Pro Glu Glu Thr Asn Tyr Lys Ala
        195                 200                 205 gtt tct tat cat gcc tca ggc cac agt gtt gcc tac aag cct gga ggc     672
```

```
              Val Ser Tyr His Ala Ser Gly His Ser Val Ala Tyr Lys Pro Gly Gly
                  210                 215                 220 ttc aag gcc agc act ggc ttt ggg tcc aac acc aaa aac aag aag ata        720
Phe Lys Ala Ser Thr Gly Phe Gly Ser Asn Thr Lys Asn Lys Lys Ile
225                 230                 235                 240 tac gat gga ggt gcc cgc aca gag gac gag gtc tac aac tcg aac aaa        768
Tyr Asp Gly Gly Ala Arg Thr Glu Asp Glu Val Tyr Asn Ser Asn Lys
                245                 250                 255 gac agc cag agt gaa ggg act gcg cag ttg gac agc att ggc ttc agc        816
Asp Ser Gln Ser Glu Gly Thr Ala Gln Leu Asp Ser Ile Gly Phe Ser
            260                 265                 270 ata atc agg aaa tgc atc cat gct gtg gaa acc aga ggg atc aac gag        864
Ile Ile Arg Lys Cys Ile His Ala Val Glu Thr Arg Gly Ile Asn Glu
        275                 280                 285 caa ggg ctg tat cga att gtg ggt gtc aac tcc aga gtg cag aag ttg        912
Gln Gly Leu Tyr Arg Ile Val Gly Val Asn Ser Arg Val Gln Lys Leu
    290                 295                 300 ctg agt gtc ctg atg gac ccc aag act gct tct gag aca gaa aca gat        960
Leu Ser Val Leu Met Asp Pro Lys Thr Ala Ser Glu Thr Glu Thr Asp
305                 310                 315                 320 atc tgt gct gaa tgg gag ata aag acc atc act agt gct ctg aag acc       1008
Ile Cys Ala Glu Trp Glu Ile Lys Thr Ile Thr Ser Ala Leu Lys Thr
                325                 330                 335 tac cta aga atg ctt cca gga cca ctc atg atg tac cag ttt caa aga       1056
Tyr Leu Arg Met Leu Pro Gly Pro Leu Met Met Tyr Gln Phe Gln Arg
                340                 345                 350 agt ttc atc aaa gca gca aaa ctg gag aac cag gag tct cgg gtc tct       1104
Ser Phe Ile Lys Ala Ala Lys Leu Glu Asn Gln Glu Ser Arg Val Ser
            355                 360                 365 gaa atc cac agc ctt gtt cat cgg ctc cca gag aaa aat cgg cag atg       1152
Glu Ile His Ser Leu Val His Arg Leu Pro Glu Lys Asn Arg Gln Met
        370                 375                 380 tta cag ctg ctc atg aac cac ttg gca aat gtt gct aac aac cac aag       1200
Leu Gln Leu Leu Met Asn His Leu Ala Asn Val Ala Asn Asn His Lys
385                 390                 395                 400 cag aat ttg atg acg gtg gca aac ctt ggt gtg gtg ttt gga ccc act       1248
Gln Asn Leu Met Thr Val Ala Asn Leu Gly Val Val Phe Gly Pro Thr
                405                 410                 415 ctg ctg agg cct cag gaa gaa aca gta gca gcc atc atg gac atc aaa       1296
Leu Leu Arg Pro Gln Glu Glu Thr Val Ala Ala Ile Met Asp Ile Lys
                420                 425                 430 ttt cag aac att gtc att gag atc cta ata gaa aac cac gaa aag ata       1344
Phe Gln Asn Ile Val Ile Glu Ile Leu Ile Glu Asn His Glu Lys Ile
            435                 440                 445 ttt aac acc gtg ccc gat atg cct ctc acc aat gcc cag ctg cac ctg       1392
Phe Asn Thr Val Pro Asp Met Pro Leu Thr Asn Ala Gln Leu His Leu
450                 455                 460 tct cgg aag aag agc agt gac tcc aag ccc ccg tcc tgc agc gag agg       1440
Ser Arg Lys Lys Ser Ser Asp Ser Lys Pro Pro Ser Cys Ser Glu Arg
465                 470                 475                 480 ccc ctg acg ctc ttc cac acc gtt cag tca aca gag aaa cag gaa caa       1488
Pro Leu Thr Leu Phe His Thr Val Gln Ser Thr Glu Lys Gln Glu Gln
                485                 490                 495 agg aac agc atc atc aac tcc agt ttg gaa tct gtc tca tca aat cca       1536
Arg Asn Ser Ile Ile Asn Ser Ser Leu Glu Ser Val Ser Ser Asn Pro
            500                 505                 510 aac agc atc ctt aat tcc agc agc agc tta cag ccc aac atg aac tcc       1584
Asn Ser Ile Leu Asn Ser Ser Ser Ser Leu Gln Pro Asn Met Asn Ser
        515                 520                 525
```

-continued

| | | | | | | | | | | | | | | | | |
|---|---|---|---|---|---|---|---|---|---|---|---|---|---|---|---|---|
| agt | gac | cca | gac | ctg | gct | gtg | gtc | aaa | ccc | acc | cgg | ccc | aac | tca | ctc | 1632 |
| Ser | Asp | Pro | Asp | Leu | Ala | Val | Val | Lys | Pro | Thr | Arg | Pro | Asn | Ser | Leu | |
| | 530 | | | | 535 | | | | | 540 | | | | | | |
| ccc | ccg | aat | cca | agc | cca | act | tca | ccc | ctc | tcg | cca | tct | tgg | ccc | atg | 1680 |
| Pro | Pro | Asn | Pro | Ser | Pro | Thr | Ser | Pro | Leu | Ser | Pro | Ser | Trp | Pro | Met | |
| 545 | | | | | 550 | | | | | 555 | | | | | 560 | |
| ttc | tcg | gcg | cca | tcc | agc | cct | atg | ccc | acc | tca | tcc | acg | tcc | agc | gac | 1728 |
| Phe | Ser | Ala | Pro | Ser | Ser | Pro | Met | Pro | Thr | Ser | Ser | Thr | Ser | Ser | Asp | |
| | | | | 565 | | | | | 570 | | | | | 575 | | |
| tca | tcc | ccc | gtc | agg | tct | gtt | gca | ggg | ttt | gtt | tgg | ttt | tct | gtt | gct | 1776 |
| Ser | Ser | Pro | Val | Arg | Ser | Val | Ala | Gly | Phe | Val | Trp | Phe | Ser | Val | Ala | |
| | | | 580 | | | | | 585 | | | | | 590 | | | |
| gcc | gtt | gtt | ctc | tca | ttg | gct | cgg | tcc | tct | ctt | cat | gca | gtg | ttc | agc | 1824 |
| Ala | Val | Val | Leu | Ser | Leu | Ala | Arg | Ser | Ser | Leu | His | Ala | Val | Phe | Ser | |
| | | 595 | | | | | 600 | | | | | 605 | | | | |
| ctc | ctc | gtc | aac | ttt | gtt | ccc | tgc | cat | cca | aac | ctg | cac | ttg | ctt | ttt | 1872 |
| Leu | Leu | Val | Asn | Phe | Val | Pro | Cys | His | Pro | Asn | Leu | His | Leu | Leu | Phe | |
| | 610 | | | | | 615 | | | | | 620 | | | | | |
| gac | agg | cca | gaa | gaa | gcg | gta | cat | gaa | gac | tcc | agc | aca | ccg | ttc | cgg | 1920 |
| Asp | Arg | Pro | Glu | Glu | Ala | Val | His | Glu | Asp | Ser | Ser | Thr | Pro | Phe | Arg | |
| 625 | | | | | 630 | | | | | 635 | | | | | 640 | |
| aag | gca | aaa | gcc | ttg | tat | gcc | tgc | aaa | gct | gaa | cat | gac | tca | gaa | ctt | 1968 |
| Lys | Ala | Lys | Ala | Leu | Tyr | Ala | Cys | Lys | Ala | Glu | His | Asp | Ser | Glu | Leu | |
| | | | | 645 | | | | | 650 | | | | | 655 | | |
| tcg | ttc | aca | gca | ggc | acg | gtc | ttc | gat | aac | gtt | cac | cca | tct | cag | gag | 2016 |
| Ser | Phe | Thr | Ala | Gly | Thr | Val | Phe | Asp | Asn | Val | His | Pro | Ser | Gln | Glu | |
| | | | 660 | | | | | 665 | | | | | 670 | | | |
| cct | ggc | tgg | ttg | gag | ggg | act | ctg | aac | gga | aag | act | ggc | ctc | atc | cct | 2064 |
| Pro | Gly | Trp | Leu | Glu | Gly | Thr | Leu | Asn | Gly | Lys | Thr | Gly | Leu | Ile | Pro | |
| | | 675 | | | | | 680 | | | | | 685 | | | | |
| gag | aat | tac | gtg | gag | ttc | ctc | taa | | | | | | | | | 2088 |
| Glu | Asn | Tyr | Val | Glu | Phe | Leu | | | | | | | | | | |
| | 690 | | | | 695 | | | | | | | | | | | |

```
<210> SEQ ID NO 6
<211> LENGTH: 695
<212> TYPE: PRT
<213> ORGANISM: Homo sapience

<400> SEQUENCE: 6
```

| | | | | | | | | | | | | | | |
|---|---|---|---|---|---|---|---|---|---|---|---|---|---|---|
| Met | Ala | Val | Thr | Ala | Cys | Gln | Gly | Leu | Gly | Phe | Val | Val | Ser | Leu | Ile |
| 1 | | | | 5 | | | | | 10 | | | | | 15 | |
| Gly | Ile | Ala | Gly | Ile | Ile | Ala | Ala | Thr | Cys | Met | Asp | Gln | Trp | Ser | Thr |
| | | | 20 | | | | 25 | | | | | 30 | | | |
| Gln | Asp | Leu | Tyr | Asn | Asn | Pro | Val | Thr | Ala | Val | Phe | Asn | Tyr | Gln | Gly |
| | | 35 | | | | | 40 | | | | | 45 | | | |
| Leu | Trp | Arg | Ser | Cys | Val | Arg | Glu | Ser | Ser | Gly | Phe | Thr | Glu | Cys | Arg |
| | 50 | | | | | 55 | | | | | 60 | | | | |
| Gly | Tyr | Phe | Thr | Leu | Leu | Gly | Leu | Pro | Ala | Met | Leu | Gln | Ala | Val | Arg |
| 65 | | | | | 70 | | | | | 75 | | | | | 80 |
| Ala | Leu | Met | Ile | Val | Gly | Ile | Val | Leu | Gly | Ala | Ile | Gly | Leu | Leu | Val |
| | | | | 85 | | | | | 90 | | | | | 95 | |
| Ser | Ile | Phe | Ala | Leu | Lys | Cys | Ile | Arg | Ile | Gly | Ser | Met | Glu | Asp | Ser |
| | | | 100 | | | | 105 | | | | | 110 | | | |
| Ala | Lys | Ala | Asn | Met | Thr | Leu | Thr | Ser | Gly | Ile | Met | Phe | Ile | Val | Ser |
| | | 115 | | | | | 120 | | | | | 125 | | | |
| Gly | Leu | Cys | Ala | Ile | Ala | Gly | Val | Ser | Val | Phe | Ala | Asn | Met | Leu | Val |
| | 130 | | | | | 135 | | | | | 140 | | | | |

-continued

```
Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Tyr Asn Ser Asn Lys
                245                 250                 255

Asp Ser Gln Ser Glu Gly Thr Ala Gln Leu Asp Ser Ile Gly Phe Ser
            260                 265                 270

Ile Ile Arg Lys Cys Ile His Ala Val Glu Thr Arg Gly Ile Asn Glu
        275                 280                 285

Gln Gly Leu Tyr Arg Ile Val Gly Val Asn Ser Arg Val Gln Lys Leu
    290                 295                 300

Leu Ser Val Leu Met Asp Pro Lys Thr Ala Ser Glu Thr Glu Thr Asp
305                 310                 315                 320

Ile Cys Ala Glu Trp Glu Ile Lys Thr Ile Thr Ser Ala Leu Lys Thr
                325                 330                 335

Tyr Leu Arg Met Leu Pro Gly Pro Leu Met Met Tyr Gln Phe Gln Arg
            340                 345                 350

Ser Phe Ile Lys Ala Ala Lys Leu Glu Asn Gln Glu Ser Arg Val Ser
        355                 360                 365

Glu Ile His Ser Leu Val His Arg Leu Pro Glu Lys Asn Arg Gln Met
    370                 375                 380

Leu Gln Leu Leu Met Asn His Leu Ala Asn Val Ala Asn Asn His Lys
385                 390                 395                 400

Gln Asn Leu Met Thr Val Ala Asn Leu Gly Val Val Phe Gly Pro Thr
                405                 410                 415

Leu Leu Arg Pro Gln Glu Glu Thr Val Ala Ala Ile Met Asp Ile Lys
            420                 425                 430

Phe Gln Asn Ile Val Ile Glu Ile Leu Ile Glu Asn His Glu Lys Ile
        435                 440                 445

Phe Asn Thr Val Pro Asp Met Pro Leu Thr Asn Ala Gln Leu His Leu
    450                 455                 460

Ser Arg Lys Lys Ser Ser Asp Ser Lys Pro Pro Ser Cys Ser Glu Arg
465                 470                 475                 480

Pro Leu Thr Leu Phe His Thr Val Gln Ser Thr Glu Lys Gln Glu Gln
                485                 490                 495

Arg Asn Ser Ile Ile Asn Ser Ser Leu Glu Ser Val Ser Ser Asn Pro
            500                 505                 510

Asn Ser Ile Leu Asn Ser Ser Ser Leu Gln Pro Asn Met Asn Ser
        515                 520                 525

Ser Asp Pro Asp Leu Ala Val Val Lys Pro Thr Arg Pro Asn Ser Leu
    530                 535                 540

Pro Pro Asn Pro Ser Pro Thr Ser Pro Leu Ser Pro Ser Trp Pro Met
545                 550                 555                 560

Phe Ser Ala Pro Ser Ser Pro Met Pro Thr Ser Ser Thr Ser Ser Asp
```

```
                    565                 570                 575
Ser Ser Pro Val Arg Ser Val Ala Gly Phe Val Trp Phe Ser Val Ala
            580                 585                 590

Ala Val Val Leu Ser Leu Ala Arg Ser Ser Leu His Ala Val Phe Ser
            595                 600                 605

Leu Leu Val Asn Phe Val Pro Cys His Pro Asn Leu His Leu Leu Phe
            610                 615                 620

Asp Arg Pro Glu Glu Ala Val His Glu Asp Ser Ser Thr Pro Phe Arg
625                 630                 635                 640

Lys Ala Lys Ala Leu Tyr Ala Cys Lys Ala Glu His Asp Ser Glu Leu
                645                 650                 655

Ser Phe Thr Ala Gly Thr Val Phe Asp Asn Val His Pro Ser Gln Glu
            660                 665                 670

Pro Gly Trp Leu Glu Gly Thr Leu Asn Gly Lys Thr Gly Leu Ile Pro
            675                 680                 685

Glu Asn Tyr Val Glu Phe Leu
            690                 695

<210> SEQ ID NO 7
<211> LENGTH: 1923
<212> TYPE: DNA
<213> ORGANISM: Homo sapience
<220> FEATURE:
<221> NAME/KEY: CDS
<222> LOCATION: (1)..(1920)

<400> SEQUENCE: 7 atg gcc gtg act gcc tgt cag ggc ttg ggg ttc gtg gtt tca ctg att      48
Met Ala Val Thr Ala Cys Gln Gly Leu Gly Phe Val Val Ser Leu Ile
1               5                   10                  15 ggg att gcg ggc atc att gct gcc acc tgc atg gac cag tgg agc acc      96
Gly Ile Ala Gly Ile Ile Ala Ala Thr Cys Met Asp Gln Trp Ser Thr
            20                  25                  30 caa gac ttg tac aac aac ccc gta aca gct gtt ttc aac tac cag ggg     144
Gln Asp Leu Tyr Asn Asn Pro Val Thr Ala Val Phe Asn Tyr Gln Gly
        35                  40                  45 ctg tgg cgc tcc tgt gtc cga gag agc tct ggc ttc acc gag tgc cgg     192
Leu Trp Arg Ser Cys Val Arg Glu Ser Ser Gly Phe Thr Glu Cys Arg
    50                  55                  60 ggc tac ttc acc ctg ctg ggg ctg cca gcc atg ctg cag gca gtg cga     240
Gly Tyr Phe Thr Leu Leu Gly Leu Pro Ala Met Leu Gln Ala Val Arg
65                  70                  75                  80 gcc ctg atg atc gta ggc atc gtc ctg ggt gcc att ggc ctc ctg gta     288
Ala Leu Met Ile Val Gly Ile Val Leu Gly Ala Ile Gly Leu Leu Val
                85                  90                  95 tcc atc ttt gcc ctg aaa tgc atc cgc att ggc agc atg gag gac tct     336
Ser Ile Phe Ala Leu Lys Cys Ile Arg Ile Gly Ser Met Glu Asp Ser
            100                 105                 110 gcc aaa gcc aac atg aca ctg acc tcc ggg atc atg ttc att gtc tca     384
Ala Lys Ala Asn Met Thr Leu Thr Ser Gly Ile Met Phe Ile Val Ser
        115                 120                 125 ggt ctt tgt gca att gct gga gtg tct gtg ttt gcc aac atg ctg gtg     432
Gly Leu Cys Ala Ile Ala Gly Val Ser Val Phe Ala Asn Met Leu Val
    130                 135                 140 act aac ttc tgg atg tcc aca gct aac atg tac acc ggc atg ggt ggg     480
Thr Asn Phe Trp Met Ser Thr Ala Asn Met Tyr Thr Gly Met Gly Gly
145                 150                 155                 160 atg gtg cag act gtt cag acc agg tac aca ttt ggt gcg gct ctg ttc     528
Met Val Gln Thr Val Gln Thr Arg Tyr Thr Phe Gly Ala Ala Leu Phe
```

-continued

```
                 165                 170                 175
gtg ggc tgg gtc gct gga ggc ctc aca cta att ggg ggt gtg atg atg      576
Val Gly Trp Val Ala Gly Gly Leu Thr Leu Ile Gly Gly Val Met Met
            180                 185                 190 tgc atc gcc tgc cgg ggc ctg gca cca gaa gaa acc aac tac aaa gcc      624
Cys Ile Ala Cys Arg Gly Leu Ala Pro Glu Glu Thr Asn Tyr Lys Ala
        195                 200                 205 gtt tct tat cat gcc tca ggc cac agt gtt gcc tac aag cct gga ggc      672
Val Ser Tyr His Ala Ser Gly His Ser Val Ala Tyr Lys Pro Gly Gly
    210                 215                 220 ttc aag gcc agc act ggc ttt ggg tcc aac acc aaa aac aag aag ata      720
Phe Lys Ala Ser Thr Gly Phe Gly Ser Asn Thr Lys Asn Lys Lys Ile
225                 230                 235                 240 tac gat gga ggt gcc cgc aca gag gac gag gtc tac aac tcg aac aaa      768
Tyr Asp Gly Gly Ala Arg Thr Glu Asp Glu Val Tyr Asn Ser Asn Lys
                245                 250                 255 gac agc cag agt gaa ggg act gcg cag ttg gac agc att ggc ttc agc      816
Asp Ser Gln Ser Glu Gly Thr Ala Gln Leu Asp Ser Ile Gly Phe Ser
            260                 265                 270 ata atc agg aaa tgc atc cat gct gtg gaa acc aga ggg atc aac gag      864
Ile Ile Arg Lys Cys Ile His Ala Val Glu Thr Arg Gly Ile Asn Glu
        275                 280                 285 caa ggg ctg tat cga att gtg ggt gtc aac tcc aga gtg cag aag ttg      912
Gln Gly Leu Tyr Arg Ile Val Gly Val Asn Ser Arg Val Gln Lys Leu
    290                 295                 300 ctg agt gtc ctg atg gac ccc aag act gct tct gag aca gaa aca gat      960
Leu Ser Val Leu Met Asp Pro Lys Thr Ala Ser Glu Thr Glu Thr Asp
305                 310                 315                 320 atc tgt gct gaa tgg gag ata aag acc atc act agt gct ctg aag acc     1008
Ile Cys Ala Glu Trp Glu Ile Lys Thr Ile Thr Ser Ala Leu Lys Thr
                325                 330                 335 tac cta aga atg ctt cca gga cca ctc atg atg tac cag ttt caa aga     1056
Tyr Leu Arg Met Leu Pro Gly Pro Leu Met Met Tyr Gln Phe Gln Arg
            340                 345                 350 agt ttc atc aaa gca gca aaa ctg gag aac cag gag tct cgg gtc tct     1104
Ser Phe Ile Lys Ala Ala Lys Leu Glu Asn Gln Glu Ser Arg Val Ser
        355                 360                 365 gaa atc cac agc ctt gtt cat cgg ctc cca gag aaa aat cgg cag atg     1152
Glu Ile His Ser Leu Val His Arg Leu Pro Glu Lys Asn Arg Gln Met
    370                 375                 380 tta cag ctg ctc atg aac cac ttg gca aat gtt gct aac aac cac aag     1200
Leu Gln Leu Leu Met Asn His Leu Ala Asn Val Ala Asn Asn His Lys
385                 390                 395                 400 cag aat ttg atg acg gtg gca aac ctt ggt gtg gtt ttt gga ccc act     1248
Gln Asn Leu Met Thr Val Ala Asn Leu Gly Val Val Phe Gly Pro Thr
                405                 410                 415 ctg ctg agg cct cag gaa gaa aca gta gca gcc atc atg gac atc aaa     1296
Leu Leu Arg Pro Gln Glu Glu Thr Val Ala Ala Ile Met Asp Ile Lys
            420                 425                 430 ttt cag aac att gtc att gag atc cta ata gaa aac cac gaa aag ata     1344
Phe Gln Asn Ile Val Ile Glu Ile Leu Ile Glu Asn His Glu Lys Ile
        435                 440                 445 ttt aac acc gtg ccc gat atg cct ctc acc aat gcc cag ctg cac ctg     1392
Phe Asn Thr Val Pro Asp Met Pro Leu Thr Asn Ala Gln Leu His Leu
    450                 455                 460 tct cgg aag aag agc agt gac tcc aag ccc ccg tcc tgc agc gag agg     1440
Ser Arg Lys Lys Ser Ser Asp Ser Lys Pro Pro Ser Cys Ser Glu Arg
465                 470                 475                 480 ccc ctg acg ctc ttc cac acc gtt cag tca aca gag aaa cag gaa caa     1488
Pro Leu Thr Leu Phe His Thr Val Gln Ser Thr Glu Lys Gln Glu Gln
```

```
Pro Leu Thr Leu Phe His Thr Val Gln Ser Thr Glu Lys Gln Glu Gln
                485                 490                 495 agg aac agc atc atc aac tcc agt ttg gaa tct gtc tca tca aat cca      1536
Arg Asn Ser Ile Ile Asn Ser Ser Leu Glu Ser Val Ser Ser Asn Pro
            500                 505                 510 aac agc atc ctt aat tcc agc agc agc tta cag ccc aac atg aac tcc      1584
Asn Ser Ile Leu Asn Ser Ser Ser Ser Leu Gln Pro Asn Met Asn Ser
            515                 520                 525 agt gac cca gac ctg gct gtg gtc aaa ccc acc cgg ccc aac tca ctc      1632
Ser Asp Pro Asp Leu Ala Val Val Lys Pro Thr Arg Pro Asn Ser Leu
530                 535                 540 ccc ccg aat cca agc cca act tca ccc ctc tcg cca tct tgg ccc atg      1680
Pro Pro Asn Pro Ser Pro Thr Ser Pro Leu Ser Pro Ser Trp Pro Met
545                 550                 555                 560 ttc tcg gcg cca tcc agc cct atg ccc acc tca tcc acg tcc agc gac      1728
Phe Ser Ala Pro Ser Ser Pro Met Pro Thr Ser Ser Thr Ser Ser Asp
                565                 570                 575 tca tcc ccc gtc agc aca ccg ttc cgg aag gca aaa gcc ttg tat gcc      1776
Ser Ser Pro Val Ser Thr Pro Phe Arg Lys Ala Lys Ala Leu Tyr Ala
                580                 585                 590 tgc aaa gct gaa cat gac tca gaa ctt tcg ttc aca gca ggc acg gtc      1824
Cys Lys Ala Glu His Asp Ser Glu Leu Ser Phe Thr Ala Gly Thr Val
            595                 600                 605 ttc gat aac gtt cac cca tct cag gag cct ggc tgg ttg gag ggg act      1872
Phe Asp Asn Val His Pro Ser Gln Glu Pro Gly Trp Leu Glu Gly Thr
610                 615                 620 ctg aac gga aag act ggc ctc atc cct gag aat tac gtg gag ttc ctc      1920
Leu Asn Gly Lys Thr Gly Leu Ile Pro Glu Asn Tyr Val Glu Phe Leu
625                 630                 635                 640 taa                                                                  1923

<210> SEQ ID NO 8
<211> LENGTH: 640
<212> TYPE: PRT
<213> ORGANISM: Homo sapience

<400> SEQUENCE: 8

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160
```

```
Met Val Gln Thr Val Gln Thr Arg Tyr Thr Phe Gly Ala Ala Leu Phe
            165                 170                 175
Val Gly Trp Val Ala Gly Gly Leu Thr Leu Ile Gly Val Met Met
        180                 185                 190
Cys Ile Ala Cys Arg Gly Leu Ala Pro Glu Glu Thr Asn Tyr Lys Ala
            195                 200                 205
Val Ser Tyr His Ala Ser Gly His Ser Val Ala Tyr Lys Pro Gly Gly
        210                 215                 220
Phe Lys Ala Ser Thr Gly Phe Gly Ser Asn Thr Lys Asn Lys Lys Ile
225                 230                 235                 240
Tyr Asp Gly Gly Ala Arg Thr Glu Asp Glu Val Tyr Asn Ser Asn Lys
                245                 250                 255
Asp Ser Gln Ser Glu Gly Thr Ala Gln Leu Asp Ser Ile Gly Phe Ser
            260                 265                 270
Ile Ile Arg Lys Cys Ile His Ala Val Glu Thr Arg Gly Ile Asn Glu
        275                 280                 285
Gln Gly Leu Tyr Arg Ile Val Gly Val Asn Ser Arg Val Gln Lys Leu
        290                 295                 300
Leu Ser Val Leu Met Asp Pro Lys Thr Ala Ser Glu Thr Glu Thr Asp
305                 310                 315                 320
Ile Cys Ala Glu Trp Glu Ile Lys Thr Ile Thr Ser Ala Leu Lys Thr
                325                 330                 335
Tyr Leu Arg Met Leu Pro Gly Pro Leu Met Met Tyr Gln Phe Gln Arg
            340                 345                 350
Ser Phe Ile Lys Ala Ala Lys Leu Glu Asn Gln Glu Ser Arg Val Ser
        355                 360                 365
Glu Ile His Ser Leu Val His Arg Leu Pro Glu Lys Asn Arg Gln Met
        370                 375                 380
Leu Gln Leu Leu Met Asn His Leu Ala Asn Val Ala Asn His His Lys
385                 390                 395                 400
Gln Asn Leu Met Thr Val Ala Asn Leu Gly Val Val Phe Gly Pro Thr
                405                 410                 415
Leu Leu Arg Pro Gln Glu Glu Thr Val Ala Ala Ile Met Asp Ile Lys
            420                 425                 430
Phe Gln Asn Ile Val Ile Glu Ile Leu Ile Glu Asn His Glu Lys Ile
        435                 440                 445
Phe Asn Thr Val Pro Asp Met Pro Leu Thr Asn Ala Gln Leu His Leu
        450                 455                 460
Ser Arg Lys Lys Ser Ser Asp Ser Lys Pro Pro Ser Cys Ser Glu Arg
465                 470                 475                 480
Pro Leu Thr Leu Phe His Thr Val Gln Ser Thr Glu Lys Gln Glu Gln
                485                 490                 495
Arg Asn Ser Ile Ile Asn Ser Ser Leu Glu Ser Val Ser Ser Asn Pro
            500                 505                 510
Asn Ser Ile Leu Asn Ser Ser Ser Leu Gln Pro Asn Met Asn Ser
        515                 520                 525
Ser Asp Pro Asp Leu Ala Val Val Lys Pro Thr Arg Pro Asn Ser Leu
        530                 535                 540
Pro Pro Asn Pro Ser Pro Thr Ser Pro Leu Pro Ser Trp Pro Met
545                 550                 555                 560
Phe Ser Ala Pro Ser Pro Met Pro Thr Ser Ser Thr Ser Ser Asp
                565                 570                 575
Ser Ser Pro Val Ser Thr Pro Phe Arg Lys Ala Lys Ala Leu Tyr Ala
```

```
                580             585             590
Cys Lys Ala Glu His Asp Ser Glu Leu Ser Phe Thr Ala Gly Thr Val
        595                 600                 605

Phe Asp Asn Val His Pro Ser Gln Glu Pro Gly Trp Leu Glu Gly Thr
        610                 615                 620

Leu Asn Gly Lys Thr Gly Leu Ile Pro Glu Asn Tyr Val Glu Phe Leu
625                 630                 635                 640
```

```
<210> SEQ ID NO 9
<211> LENGTH: 18
<212> TYPE: DNA
<213> ORGANISM: Homo sapience

<400> SEQUENCE: 9
gtgtttgcca acatgctg                                               18

<210> SEQ ID NO 10
<211> LENGTH: 21
<212> TYPE: DNA
<213> ORGANISM: Homo sapience

<400> SEQUENCE: 10
tgacagctca ggtcacagtc c                                           21

<210> SEQ ID NO 11
<211> LENGTH: 18
<212> TYPE: DNA
<213> ORGANISM: Homo sapience

<400> SEQUENCE: 11
ctggttctcc agttttgc                                               18

<210> SEQ ID NO 12
<211> LENGTH: 18
<212> TYPE: DNA
<213> ORGANISM: Homo sapience

<400> SEQUENCE: 12
aggtacacat ttggtgcg                                               18

<210> SEQ ID NO 13
<211> LENGTH: 20
<212> TYPE: DNA
<213> ORGANISM: Homo sapience

<400> SEQUENCE: 13
ctctggatgg ggactgacct                                             20

<210> SEQ ID NO 14
<211> LENGTH: 18
<212> TYPE: DNA
<213> ORGANISM: Homo sapience

<400> SEQUENCE: 14
cctggaagca ttcttagg                                               18

<210> SEQ ID NO 15
<211> LENGTH: 20
<212> TYPE: DNA
<213> ORGANISM: Homo sapience

<400> SEQUENCE: 15
```

```
gaagtccctt gccatcctaa                                              20

<210> SEQ ID NO 16
<211> LENGTH: 20
<212> TYPE: DNA
<213> ORGANISM: Homo sapience

<400> SEQUENCE: 16
gcacgaaggc tcatcattca                                              20

<210> SEQ ID NO 17
<211> LENGTH: 80
<212> TYPE: DNA
<213> ORGANISM: Homo sapiens

<400> SEQUENCE: 17
caagaagata tacgatggag gtgcccgcac agaggacgag gtctacaact cgaacaaaga  60
cagccagagt gaagggactg                                              80

<210> SEQ ID NO 18
<211> LENGTH: 80
<212> TYPE: DNA
<213> ORGANISM: Homo sapiens

<400> SEQUENCE: 18
caagaagata tacgatggag gtgcccgcac agaggacgag ggtgatttca cctggaacag  60
catgccaggc cgcagtgtac                                              80

<210> SEQ ID NO 19
<211> LENGTH: 80
<212> TYPE: DNA
<213> ORGANISM: Homo sapiens

<400> SEQUENCE: 19
caagaagata tacgatggag gtgcccgcac agaggacgag ggtgatttca cctggaacag  60
catgtcaggc cgcagtgtac                                              80

<210> SEQ ID NO 20
<211> LENGTH: 80
<212> TYPE: DNA
<213> ORGANISM: Homo sapiens

<400> SEQUENCE: 20
caagaagata tacgatggag gtgcccgcac agaggacgag ggtgatttca cccggaacag  60
catgtcaggc cgcagtgtac                                              80

<210> SEQ ID NO 21
<211> LENGTH: 80
<212> TYPE: DNA
<213> ORGANISM: Homo sapiens

<400> SEQUENCE: 21
caagaagata tacgatggag gtgcccgcac agaggacgaa ggtgatttca cctggaacag  60
catgtcaggc cgcagtgtac                                              80
```

UNITED STATES PATENT AND TRADEMARK OFFICE
CERTIFICATE OF CORRECTION

PATENT NO. : 11,053,553 B2
APPLICATION NO. : 16/324366
DATED : July 6, 2021
INVENTOR(S) : Hiroki Sasaki Page 1 of 1

It is certified that error appears in the above-identified patent and that said Letters Patent is hereby corrected as shown below:

On the Title Page

Item (30) Foreign Application Priority Data should read as follows:
Aug. 10, 2016 (JP) ..........................2016-157167
Nov. 14, 2016 (JP) ..........................2016-221434

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*